(12) United States Patent
Miralles et al.

(10) Patent No.: US 8,545,816 B2
(45) Date of Patent: Oct. 1, 2013

(54) BENZOIC ACID ESTER COMPOUNDS, COMPOSITIONS, USES AND METHODS RELATED THERETO

(75) Inventors: Ricardo Miralles, Barcelona (ES); Santiago Nonell, Barcelona (ES); Manuel M. Raga, Barcelona (ES); Antonio Giuglietta, Barcelona (ES); Jordi Teixidó, Barcelona (ES)

(73) Assignee: Ferrer Internacional, S.A., Barcelona (ES)

( * ) Notice: Subject to any disclaimer, the term of this patent is extended or adjusted under 35 U.S.C. 154(b) by 1642 days.

(21) Appl. No.: 11/886,792

(22) PCT Filed: Mar. 20, 2006

(86) PCT No.: PCT/EP2006/060886
§ 371 (c)(1),
(2), (4) Date: Dec. 18, 2007

(87) PCT Pub. No.: WO2006/100225
PCT Pub. Date: Sep. 28, 2006

(65) Prior Publication Data
US 2008/0206158 A1 Aug. 28, 2008

(30) Foreign Application Priority Data
Mar. 21, 2005 (EP) .................................. 05102228

(51) Int. Cl.
*A61K 9/10* (2006.01)
*A61K 9/02* (2006.01)
*A01N 37/00* (2006.01)

(52) U.S. Cl.
USPC ................ 424/45; 424/64; 424/60; 514/576; 514/428

(58) Field of Classification Search
USPC ..................... 424/64, 60, 45; 514/576, 428
See application file for complete search history.

(56) References Cited

U.S. PATENT DOCUMENTS

| | | | |
|---|---|---|---|
| 2,811,460 A | 10/1957 | Meyer et al. | |
| 3,033,814 A | 5/1962 | Tholstrup | |
| 3,519,599 A | 7/1970 | Newland et al. | |
| 3,751,563 A | 8/1973 | Richardson | |
| 4,036,951 A | 7/1977 | Halpern et al. | |
| 4,426,386 A * | 1/1984 | Arvidsson et al. ............ | 514/317 |

FOREIGN PATENT DOCUMENTS

| | | |
|---|---|---|
| CN | 1072675 A | 6/1993 |
| DE | 1936280 A1 | 1/1970 |
| DE | 268933 A1 | 6/1989 |
| ES | 369717 A1 | 6/1971 |
| FR | 2800991 A1 | 5/2001 |
| GB | 860939 | 2/1961 |
| JP | 57-142392 A | 9/1982 |
| JP | 61-16258 A | 4/1986 |
| JP | 61293952 A * | 12/1986 |
| JP | 4-210660 A | 7/1992 |
| JP | 11-279018 A | 10/1999 |
| JP | 2000-319628 A | 11/2000 |
| JP | 2002-53527 A | 2/2002 |
| JP | 2005-15449 A | 1/2005 |
| WO | WO9925191 * | 5/1999 |
| WO | WO 02/095393 A2 | 11/2002 |

OTHER PUBLICATIONS

Ruppin et al.,Tetrahedron Letters, vol. 27, No. 52, pp. 6323-6324, 1986.*
Yanagisawa et al. (Chem. Pharm. Bull 48(11) 1838-1840 , 2000).*
Yanagisawa et al., "Aldol Reaction of Enol Esters Catalyzed by Cationic Species Paired with Tetrakis(pentafluorophenyl)borate," Chem. Pharm. Bull., vol. 48, No. 11, 2000, pp. 1838-1840, XP-001208246.
Huh et al., "Kinetics and mechanism of the hydrolysis of enol ester in strong acid solution," Journal of the Korean Chemical Society, vol. 38, No. 5, 1994, pp. 391-396, XP002363980.
Ruppin et al., "Synthesis of Enol Esters from Terminal Alkynes Catalyzed by Ruthenium Complexes," Tetrahedron Letters, vol. 27, No. 52, 1986, pp. 6323-6324, XP002363968.
Inoue et al., "Hydroxybenzoate derivatives," Jpn. Kokai Tokkyo Koho, 1987, pp. 6323-6325, XP002363981.
Asahi Kasei Amidas Co., Ltd., "Light Stabilizer," Plastic Data Book, Section 9.3, Dec. 1999, pp. 934-946 (partial translation of p. 939 provided).
European Office Action issued in European Application No. 06 725 177.7 on Apr. 17, 2013, 6 pages.
CAS Registry, Adams et al., "Preparation of aryl esters using polyphosphate ester", Accession No. 91:157491, Reg. No. 71639-97-9, 1979.
CAS Registry, Arnone et al., "Structures of the red sandalwood pigments . . .", Accession No. 82:139896, Reg. No. 55744-83-7, 1975.
CAS Registry, Coppinger et al., "Photo-Fries rearrangement of aromatic esters . . .", Accession No. 66:10375, Reg. No. 14041-73-7, 1966.

(Continued)

*Primary Examiner* — Janet Epps-Smith
*Assistant Examiner* — Courtney Brown
(74) *Attorney, Agent, or Firm* — Birch, Stewart, Kolasch & Birch, LLP

(57) ABSTRACT

Benzoic acid ester compounds of formula (I):

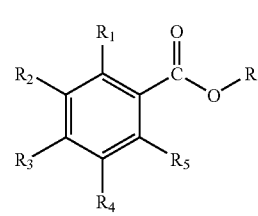

wherein R and $R_1$-$R_5$ have the meanings explained in the description, methods for producing them and use thereof in cosmetic, pharmaceutical, personal care and industrial preparations as sunscreens based on photochemical precursor properties of ultraviolet absorbers.

25 Claims, 6 Drawing Sheets

(56) References Cited

OTHER PUBLICATIONS

CAS Registry, Sartori et al., "Metal template ortho-acylation of phenols . . .", Accession No. 110:231473, Reg. No. 120781-04-6, 1988.

Russian Request of Substantive Examination, dated Jan. 19, 2011, for Russian Application No. 2007139006/04(042692).

English translation of Russian Office Action dated Oct. 18, 2012 for Russian Application No. 2007139006/04.

Meyer et al., "Ultraviolet Inhibitors for Cellulose Acetate-Butyrate Plastics—Phenyl Hydroxybenzoates, Hydroxyphenyl Benzoates, and their Methyl Ethers," Industrial and Engineering Chemistry, Jul. 1951, pp. 1585-1591(only Abstract is provided).

* cited by examiner

Des-*tert*-butylavobenzone

| $t_0$ | 0 |
| --- | --- |
| $t_1$ | 20 s |
| $t_2$ | 40 s |
| $t_3$ | 1 min |
| $t_4$ | 2 min |
| $t_5$ | 3 min |
| $t_6$ | 4 min |
| $t_7$ | 5 min |
| $t_8$ | 10 min |

Avobenzone

| $t_0$ | 0 |
|---|---|
| $t_1$ | 20 s |
| $t_2$ | 40 s |
| $t_3$ | 1 min |
| $t_4$ | 2 min |
| $t_5$ | 3 min |
| $t_6$ | 10 min |

| | Wavelength (nm) |
|---|---|
| $t_0$ | 0 |
| $t_1$ | 1 min |
| $t_2$ | 2 min |

Sulisobenzone

| $t_0$ | 0 |
|---|---|
| $t_1$ | 1 min |
| $t_2$ | 2 min |
| $t_3$ | 3 min |
| $t_4$ | 4 min |
| $t_5$ | 5 min |
| $t_6$ | 10 min |
| $t_7$ | 20 min |

Photoprotector
US 6,409,995

| | Wavelength (nm) |
|---|---|
| $t_0$ | 0 |
| $t_1$ | 2 min |
| $t_2$ | 4 min |
| $t_3$ | 6 min |
| $t_4$ | 9 min |
| $t_5$ | 20 min |

BENZOIC ACID ESTER COMPOUNDS, COMPOSITIONS, USES AND METHODS RELATED THERETO

TECHNICAL FIELD

This invention is directed to photochemical precursors of ultraviolet absorbers, especially to benzoic acid ester compounds.

BACKGROUND OF THE INVENTION

Overexposure to the sun's invisible rays, ultraviolet A (UVA, 320-400 nm) and ultraviolet B (UVB, 290-320 nm) can cause skin damage. The damage can be immediate and long-term, with effects ranging from sunburn, rashes, and cell and tissue damage to premature wrinkling and skin cancer. One particularly deadly form of skin cancer, malignant melanoma, has been on the rise in recent decades, as tanning has become more popular. Over the same period, scientists have warned that the thin layer of ozone that protects life on Earth from the sun's ultraviolet (UV) radiation is being depleted. This allows more UV radiation to get through, adding to the risk of overexposure. Indeed, many skin changes that often are identified with aging actually result from damage by too much sun.

Sunscreen is any substance or material that protects the skin from UV radiation. Sunscreens are available in the forms of topical lotion, cream, ointment, gel, or spray that can be applied to the skin; a salve or stick that can be applied to the lips, nose, and eyelids; a moistener in towelettes that can be rubbed against the skin; sunglasses that protect the eyes; and film screen that can be affixed to the windows of a car, room, or office.

Sunscreens help to prevent sunburn and reduce the harmful effects of the sun such as premature skin aging and skin cancer. But just how much protection they provide is a matter of debate. For many years, experts thought that only UVB was harmful. However, recent research suggests that UVA may be just as dangerous as UVB, although its effects may take longer to show up. In particular, UVA may play a role in causing melanoma. Most sunscreen products contain ingredients that provide adequate protection only against UVB rays. Even those labeled as "broad spectrum" sunscreens may offer only partial protection against UVA radiation. Those containing the ingredient avobenzone (4-tert-butyl-4'-methoxydibenzoylmethane) give the most protection against UVA rays.

Sunscreens should be applied between 30 minutes and 2 hours before sun exposure. In general, they should be reapplied after every 80 minutes spent in the water or when perspiring heavily or every 2 hours spent out of the water.

UVB (290-320 nm) is the most erythemogenic solar radiation reaching the surface of the earth. It is also a potent skin carcinogen in animal studies. Sun Protection Factor (SPF) indicates the degree of protection against UVB induced erythema. The US Food and Drug Administration (FDA) regulates sunscreen products as over-the-counter drugs. The Final Over-the-Counter Drug Products Monograph on Sunscreens (Federal Register 1999:64:27666-27963) established the conditions for safety, efficacy, and labeling of these products. The SPF is defined as the dose of ultraviolet radiation (UVR) required to produce 1 minimal erythema dose (MED) on protected skin after the application of 2 mg/cm$^2$ of product divided by the UVR required to produce 1 MED on unprotected skin.

All sunscreens have a SPF on their labels. The SPF represents the length of time that sunscreen-protected skin can be exposed to UV rays before a minimal redness (erythema) appears, compared to the length of time it takes on unprotected skin. In other words, it indicates how much longer the skin can be exposed to the sun before getting a sunburn. For example, without a sunscreen, an individual might get a sunburn after 20 minutes or less in the sun. By applying a sunscreen of SPF 15, the individual might spend up to 300 minutes under the sun before sunburning, that is 15 times longer than if no protection is used.

Sunscreens with SPF numbers higher than 15 may work better for people who are fair-skinned, live at high altitudes, work or play outdoors much of the day; or perspire heavily. Swimming and perspiration reduce the actual SPF value of many sunscreens, even those that are water-resistant, so it is convenient to reapply the product often.

Table 1 shows some relevant broadly used sunscreen compounds.

TABLE 1

| Drug Name | Concentration % | Absorbance | Protection nm |
|---|---|---|---|
| Avobenzone | 2-3 | UVA I[1] | 320-400 |
| Dioxybenzone | Up to 3 | UVB, UVA II[2] | 250-390 |
| Oxybenzone | Up to 6 | UVB, UVA II[2] | 270-350 |
| Sulisobenzone | Up to 10 | UVB, UVA II[2] | 260-375 |

[1]340-400 nm;
[2]320-340 nm

Avobenzone (4-tert-butyl-4'-methoxydibenzoylmethane, Parsol 1789, U.S. Pat. No. 4,387,089) provides superior protection through a large portion of the UVA range, including UVA I. Potentially a significant addition to sunscreen products for true broad-spectrum UV protection, concerns have been raised regarding its photostability and its potential to degrade other sunscreen ingredients in products in which it is used.

Dioxybenzone (2,2'-dihydroxy-4-methoxybenzophenone, U.S. Pat. No. 2,853,521) is mainly used as an UV-absorber for polymers and coatings. It is used as a stabilizer for polyester film. It is effective against UVB and some UVA light.

Oxybenzone (2-hydroxy-4-methoxybenzophenone, U.S. Pat. No. 2,773,903, U.S. Pat. No. 2,861,104, U.S. Pat. No. 2,861,105 and U.S. Pat. No. 3,073,866) absorbs well through UVA II and can be considered a broad-spectrum absorber. It significantly enhances UVB protection when used in a given formula.

Sulisobenzone (5-benzoyl-4-hydroxy-2-methoxy-benzenesulfonic acid, GB1136525) extends the coverage beyond the UVB range and into the UVA range, helping to obtain broad-spectrum sunscreen preparations.

Amino-substituted hydroxybenzophenones have been disclosed as photostable UV filters to be used in cosmetic and dermatological compositions (U.S. Pat. No. 6,409,995).

Chemical sunscreens "block" the penetration of UV radiation through the epidermis by acting as filters and absorbing and reflecting high energy UV. The sunscreen molecules absorb the high energy UV photons causing the electronic structure to move to a higher energy state. This electronic energy is dissipated by conversion to vibrational and rotational energy within the molecule, ultimately being transferred to the molecule's environment as heat.

The FDA has taken a position against the continued labeling of high SPF formulations, and has stated that the maximum SPF should not exceed 30 due to the additional costs and risks from increased concentrations of active ingredients.

This is in spite of the fact that other than the expected occurrence of occasional allergic, phototoxic, and photoallergic cutaneous reactions, there is virtually no published evidence of harm from using high SPF sunscreen formulations.

There are, in fact, a number of reasons why high SPF formulations (>30 SPF) may be the best choice for high risk individuals, especially when sun exposure is expected to be extensive. Rubbing, sweating, and water immersion diminish the effectiveness of all sunscreens, requiring frequent re-application of the product even with supposedly waterproof or sweat proof formulations. Another factor that enhances the damaging effects of lengthy exposures is a time-dependent diminution of SPF effect not related to removal of the product from rubbing or washing. Experiments in the hairless mouse model found a significant decrease in measured SPF occurring within the first few hours following sunscreen application. Studies in humans confirm that single applications of an SPF 25 sunscreen are frequently inadequate to prevent erythema, and that multiple applications are required to completely suppress erythema, even from a single day's sun exposure.

A final factor that may not be fully compensated for, even with repeated application, is the effect of multi-day UV exposures. A significant multi-day exposure to sunlight (e.g., all day Saturday and Sunday) increases the sensitivity of the skin to UV damage on the second day of exposure. This means that even if the sunscreen functions as predicted by the rated SPF to prevent erythema on the first day of exposure, the heightened sensitivity on the second and subsequent days of exposure may lead to erythema development which would not have been predicted based solely on extrapolations of the SPF. In such instances, a sunscreen with an SPF>30 may provide significantly better protection from UV damage, particularly in susceptible individuals.

Higher SPF sunscreen products have led to the use of multiple individual sunscreen agents used in combinations at maximum concentrations that may interact.

The current focus on erythema as the standard against which sunscreen potency is measured may have led to the assumption that erythema prevention is also the only important goal of sun protection, and ultimately to the FDA's position against sunscreens more potent than 30 SPF. This assumption ignores experimental evidence that significant UV-induced damage occurs prior to the development of perceptible UV-induced redness. Human research using sunburn cells as the measure of UV damage supports the existence of significant sub-erythemal DNA damage in the skin, and the value of high SPF sunscreens in preventing it.

SPF testing is designed to evaluate protection against erythema produced by natural sunlight and, therefore, denotes principally the degree of protection against UVB, since the amount of UVA received from sunlight does not produce significant erythema. The only ingredient approved by the FDA for protection against UVA radiation is avobenzone. However, if a product contains ingredients that absorb UV between 290-320 nm it can be labeled as a broad-spectrum sunscreen, meaning it will provide protection against both UVB and short wave UVA radiation.

Adverse reactions to sunscreen comprise cutaneous problems, such as allergic contact reactions, photocontact reactions, and drying or tightening of the skin. Other side effects are rare, but possible, namely acne, burning, itching, or stinging of the skin, redness or swelling of the skin, rash, with or without blisters that ooze and become crusted, pain in hairy parts of body and pus in hair follicles.

Photostability refers to the ability of a molecule to remain intact with irradiation. Poor photostability is potentially a problem with all UV filters because they are deliberately selected as UVR-absorbing molecules. This issue has been raised specifically with avobenzone, with photolysis demonstrated, especially in vitro systems, that simultaneously irradiate and measure transmittance in situ. The photostability of the molecules also depends on the solvent or the vehicle used.

Subjective irritation associated with burning or stinging without objective erythema is the most common sensitivity complaint from sunscreens. This irritation is most frequently observed in the eye area. However, persistent objective irritant contact dermatitis is a more common side effect. Virtually all sunscreen ingredients reported to cause contact allergy might be photoallergens. Sunscreen actives seem to have become the leading cause of photocontact allergic reactions. Individuals with preexisting eczematous conditions have a significant predisposition to sensitization associated with their impaired cutaneous barrier. In addition, certain antibiotics, birth control pills, diuretics, antihistamines, and antidepressants are among the commonly used drugs that can increase sensitivity to the sun's rays.

A water resistance claim of two hours means the sunscreen should retain its full SPF protection even after two hours in the water. Even water resistant, sunscreen should be reapplied after any water sports.

It is therefore desirable to discover new sunscreen compounds with a lower risk of side effects, increased photostability, and increased persistence on the skin.

The present invention provides a method for protecting a human or animal living body from ultraviolet radiation comprising treating said human or animal living body with an effective amount of a composition comprising a benzoic acid ester compound with ultraviolet absorbing properties per se susceptible to be photochemically converted in situ to another sunscreen compound with a higher UV protection. Also the present invention provides a method for protecting a material from ultraviolet radiation comprising treating said material with an effective amount of a composition comprising a benzoic acid ester compound with ultraviolet absorbing properties per se susceptible to be photochemically converted in situ to another sunscreen compound with a higher UV protection.

DETAILED DESCRIPTION OF THE INVENTION

Figure 1:
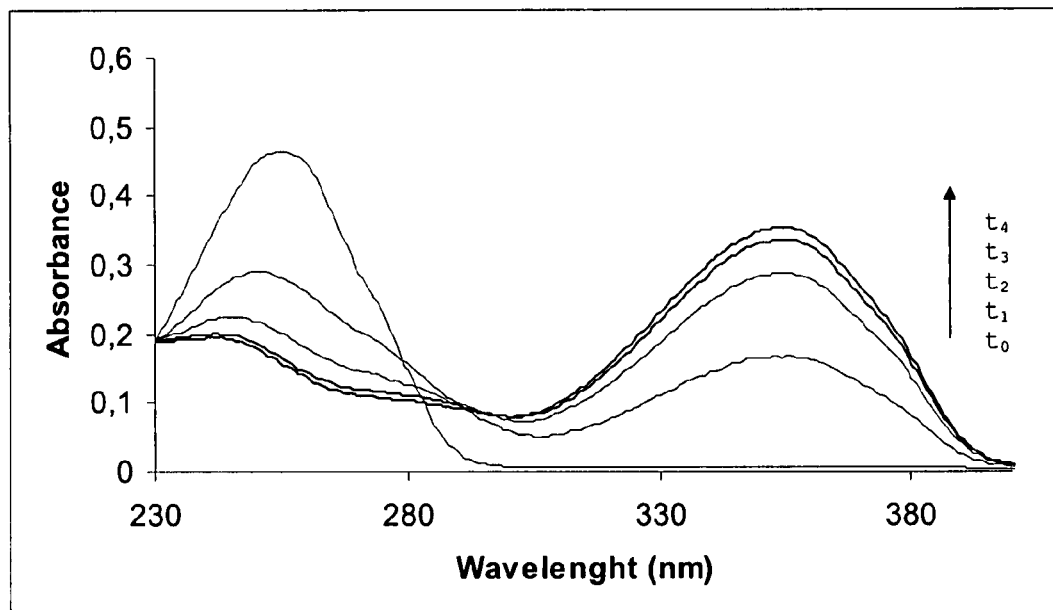
FIG. 1 shows the phototransposition kinetics of 1-phenylvinyl 4-methoxybenzoate.
Figure 1:
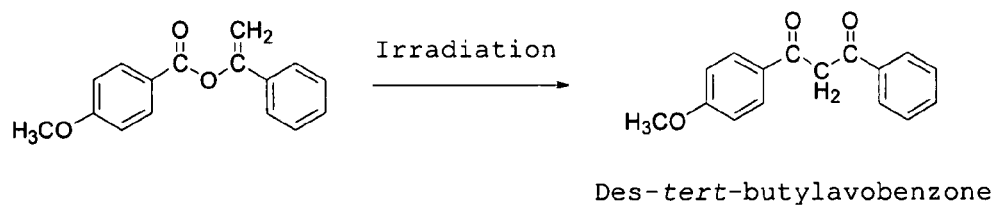

The present invention relates to a method for protecting a human or animal living body or a material from ultraviolet radiation comprising treating said human or animal living body or material with a composition comprising an effective amount of at least a benzoic acid ester compound of formula (I):

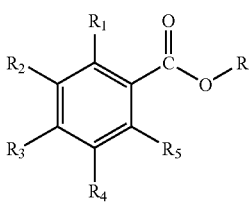

(I)

wherein $R_1$-$R_5$ are selected independently from hydrogen, $C_1$-$C_6$-alkyl, $C_3$-$C_6$-cycloalkyl, $C_1$-$C_6$-alkoxy, $C_3$-$C_6$-cycloalkoxy, hydroxy, amino, $C_1$-$C_6$-alkylamino, $C_1$-$C_6$-dialkylamino, wherein said two alkyl portions of said dialkylamino can form, together with the nitrogen atom to which they are attached, a heterocycle selected from pyrrolidine, piperidine, morpholine and piperazine optionally N-substituted by $C_1$-$C_6$-alkyl or $C_3$-$C_6$-cycloalkyl, $C_3$-$C_6$-cycloalkylamino, $C_1$-$C_6$-alkyl-$C_3$-$C_6$-cycloalkylamino and $C_3$-$C_6$-dicycloalkylamino, or two groups on adjacent ring carbons form a fused O—$(CH_2)_m$—O group wherein m is 1 or 2, or two groups on adjacent ring carbons form a fused CH=CH—CH=CH group;

R is a group selected from (i), (ii) and (iii):

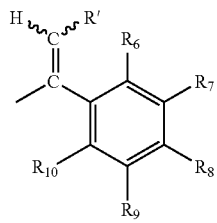

(i)

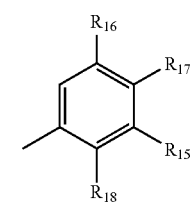

(ii)

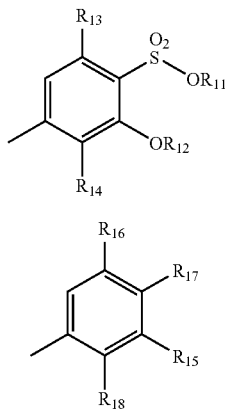

(iii)

wherein R' is selected from hydrogen, $C_1$-$C_6$-alkyl and $C_3$-$C_6$-cycloalkyl;

$R_6$-$R_{10}$ are selected independently from hydrogen, $C_1$-$C_6$-alkyl, $C_3$-$C_6$-cycloalkyl, $C_1$-$C_6$-alkoxy, $C_3$-$C_6$-cycloalkoxy, hydroxy, amino, $C_1$-$C_6$-alkylamino, $C_1$-$C_6$-dialkylamino, wherein said two alkyl portions of said dialkylamino can form, together with the nitrogen atom to which they are attached, a heterocycle selected from pyrrolidine, piperidine, morpholine and piperazine optionally N-substituted by $C_1$-$C_6$-alkyl or $C_3$-$C_6$-cycloalkyl, $C_3$-$C_6$-cycloalkylamino, $C_1$-$C_6$-alkyl-$C_3$-$C_6$-cycloalkylamino and $C_3$-$C_6$-dicycloalkylamino, or two groups on adjacent ring carbons form a fused O—$(CH_2)_n$—O group wherein n is 1 or 2, or two groups on adjacent ring carbons form a fused CH=CH—CH=CH group;

$R_{11}$ is selected from hydrogen, $C_1$-$C_6$-alkyl and $C_3$-$C_6$-cycloalkyl;

$R_{12}$ is selected from hydrogen, $C_1$-$C_6$-alkyl and $C_3$-$C_6$-cycloalkyl;

$R_{13}$ and $R_{14}$ are selected independently from hydrogen, $C_1$-$C_6$-alkyl, $C_3$-$C_6$-cycloalkyl, $C_1$-$C_6$-alkoxy, $C_3$-$C_6$-cycloalkoxy, hydroxy, amino, $C_1$-$C_6$-alkylamino, $C_1$-$C_6$-dialkylamino, wherein said two alkyl portions of said dialkylamino can form, together with the nitrogen atom to which they are attached, a heterocycle selected from pyrrolidine, piperidine, morpholine and piperazine optionally N-substituted by $C_1$-$C_6$-alkyl or $C_3$-$C_6$-cycloalkyl, $C_3$-$C_6$-cycloalkylamino, $C_1$-$C_6$-alkyl-$C_3$-$C_6$-cycloalkylamino and $C_3$-$C_6$-dicycloalkylamino;

or the group $OR_{12}$ and $R_{14}$ form a fused O—$(CH_2)_p$—O group wherein p is 1 or 2; and $R_{15}$-$R_{18}$ are selected independently from hydrogen, $C_1$-$C_6$-alkyl, $C_3$-$C_6$-cycloalkyl, $C_1$-$C_6$-alkoxy, $C_3$-$C_6$-cycloalkoxy, hydroxy, amino, $C_1$-$C_6$-alkylamino, $C_1$-$C_6$-dialkylamino, wherein said two alkyl portions of said dialkylamino can form, together with the nitrogen atom to which they are attached, a heterocycle selected from pyrrolidine, piperidine, morpholine and piperazine optionally N-substituted by $C_1$-$C_6$-alkyl or $C_3$-$C_6$-cycloalkyl, $C_3$-$C_6$-cycloalkylamino, $C_1$-$C_6$-alkyl-$C_3$-$C_6$-cycloalkylamino and $C_3$-$C_6$-dicycloalkylamino, or two groups on adjacent ring carbons form a fused O—$(CH_2)_q$—O group wherein q is 1 or 2, or two groups on adjacent ring carbons form a fused CH=CH—CH=CH group;

or a pharmaceutically acceptable salt thereof.

Some compounds included in formula (I) have not been described previously in the literature. Accordingly, the present invention relates to the new benzoic acid ester compounds of formula (Ia):

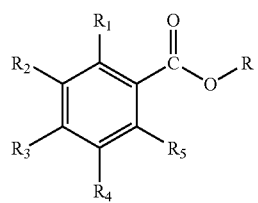

(Ia)

wherein R is a group selected from (i), (ii) and (iii):

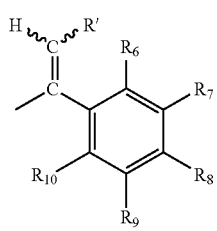

(i)

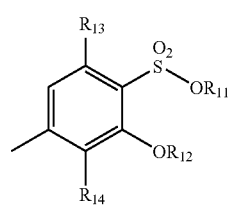

(ii)

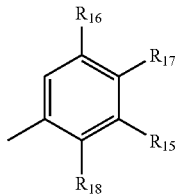

(iii)

wherein $R_1$-$R_5$ are selected independently from hydrogen, $C_1$-$C_6$-alkyl, $C_3$-$C_6$-cycloalkyl, $C_1$-$C_6$-alkoxy, $C_3$-$C_6$-cycloalkoxy, hydroxy, amino, $C_1$-$C_6$-alkylamino, $C_1$-$C_6$-dialkylamino, wherein said two alkyl portions of said dialkylamino can form, together with the nitrogen atom to which they are attached, a heterocycle selected from pyrrolidine, piperidine, morpholine and piperazine optionally N-substituted by $C_1$-$C_6$-alkyl or $C_3$-$C_6$-cycloalkyl, $C_3$-$C_6$-cycloalkylamino, $C_1$-$C_6$-alkyl-$C_3$-$C_6$-cycloalkylamino and $C_3$-$C_6$-dicycloalkylamino, or two groups on adjacent ring carbons form a fused O—$(CH_2)_m$—O group wherein m is 1 or 2, or two groups on adjacent ring carbons form a fused CH=CH—CH=CH group;

R' is hydrogen;

$R_6$-$R_{10}$ are selected independently from hydrogen, $C_1$-$C_6$-alkyl, $C_3$-$C_6$-cycloalkyl, $C_1$-$C_6$-alkoxy, $C_3$-$C_6$-cycloalkoxy, hydroxy, amino, $C_1$-$C_6$-alkylamino, $C_1$-$C_6$-dialkylamino, wherein said two alkyl portions of said dialkylamino can form, together with the nitrogen atom to which they are attached, a heterocycle selected from pyrrolidine, piperidine, morpholine and piperazine optionally N-substituted by $C_1$-$C_6$-alkyl or $C_3$-$C_6$-cycloalkyl, $C_3$-$C_6$-cycloalkylamino, $C_1$-$C_6$-alkyl-$C_3$-$C_6$-cycloalkylamino and $C_3$-$C_6$-dicycloalkylamino, or two groups on adjacent ring carbons form a fused O—$(CH_2)_n$—O group wherein n is 1 or 2, or two groups on adjacent ring carbons form a fused CH=CH—CH=CH group;

$R_{11}$ is selected from hydrogen, $C_1$-$C_6$-alkyl and $C_3$-$C_6$-cycloalkyl;

$R_{12}$ is selected from hydrogen, $C_1$-$C_6$-alkyl and $C_3$-$C_6$-cycloalkyl;

$R_{13}$ and $R_{14}$ are selected independently from hydrogen, $C_1$-$C_6$-alkyl, $C_3$-$C_6$-cycloalkyl, $C_1$-$C_6$-alkoxy, $C_3$-$C_6$-cycloalkoxy, hydroxy, amino, $C_1$-$C_6$-alkylamino, $C_1$-$C_6$-dialkylamino, wherein said two alkyl portions of said dialkylamino can form, together with the nitrogen atom to which they are attached, a heterocycle selected from pyrrolidine, piperidine, morpholine and piperazine optionally N-substituted by $C_1$-$C_6$-alkyl or $C_3$-$C_6$-cycloalkyl, $C_3$-$C_6$-cycloalkylamino, $C_1$-$C_6$-alkyl-$C_3$-$C_6$-cycloalkylamino and $C_3$-$C_6$-dicycloalkylamino;

or the group $OR_{12}$ and $R_{14}$ form a fused O—$(CH_2)_p$—O group wherein p is 1 or 2;

$R_{15}$ is selected from 1-pyrrolidinyl, 1-piperidinyl, 4-morpholinyl and 1(4)-piperazinyl optionally 4(1)-substituted by $C_1$-$C_6$-alkyl or $C_3$-$C_6$-cycloalkyl; and $R_{16}$-$R_{18}$ are selected independently from hydrogen, $C_1$-$C_6$-alkyl, $C_3$-$C_6$-cycloalkyl, $C_1$-$C_6$-alkoxy, $C_3$-$C_6$-cycloalkoxy, hydroxy, amino, $C_1$-$C_6$-alkylamino, $C_1$-$C_6$-dialkylamino, wherein said two alkyl portions of said dialkylamino can form, together with the nitrogen atom to which they are attached, a heterocycle selected from pyrrolidine, piperidine, morpholine and piperazine optionally N-substituted by $C_1$-$C_6$-alkyl or $C_3$-$C_6$-cycloalkyl, $C_3$-$C_6$-cycloalkylamino, $C_1$-$C_6$-alkyl-$C_3$-$C_6$-cycloalkylamino and $C_3$-$C_6$-dicycloalkylamino, or two groups on adjacent ring carbons form a fused O—$(CH_2)_q$—O group wherein q is 1 or 2, or two groups on adjacent ring carbons form a fused CH=CH—CH=CH group;

with the proviso that when $R_1$, $R_2$, and $R_4$-$R_{10}$ are each hydrogen, $R_3$ cannot be hydrogen or methoxy; and with the proviso that when $R_1$-$R_7$, $R_9$ and $R_{10}$ are each hydrogen, $R_8$ cannot be methyl;

or a pharmaceutically acceptable salt thereof.

More preferably the present invention relates to new benzoic acid ester compounds of formula (Ia) wherein in said compounds, when R is (i), $R_3$ is selected independently from $C_1$-$C_6$-alkyl, $C_3$-$C_6$-cycloalkyl, $C_1$-$C_6$-alkoxy and $C_3$-$C_6$-cycloalkoxy, $R_8$ is selected independently from hydrogen, $C_1$-$C_6$-alkyl, $C_3$-$C_6$-cycloalkyl, $C_1$-$C_6$-alkoxy and $C_3$-$C_6$-cycloalkoxy, and $R_1$, $R_2$, $R_4$-$R_7$, $R_9$ and $R_{10}$ are each hydrogen; when R is (ii), $R_1$-$R_5$, $R_{11}$, $R_{13}$ and $R_{14}$ are each hydrogen and $R_{12}$ is $C_1$-$C_6$-alkyl and $C_3$-$C_6$-cycloalkyl; and when R is (iii), $R_{15}$ is selected from 1-pyrrolidinyl, 1-piperidinyl, 4-morpholinyl and 1(4)-piperazinyl optionally 4(1)-substituted by $C_1$-$C_6$-alkyl or $C_3$-$C_6$-cycloalkyl and $R_{16}$-$R_{18}$ are each hydrogen;

with the proviso that when $R_1$, $R_2$, and $R_4$-$R_{10}$ are each hydrogen, $R_3$ cannot be hydrogen or methoxy; and with the proviso that when $R_1$-$R_7$, $R_9$ and $R_{10}$ are each hydrogen, $R_8$ cannot be methyl;

or a pharmaceutically acceptable salt thereof.

The term "pharmaceutically acceptable salt" used herein encompasses any salt formed from organic and inorganic acids, such as hydrobromic, hydrochloric, phosphoric, nitric, sulfuric, acetic, adipic, aspartic, benzenesulfonic, benzoic, citric, ethanesulfonic, formic, fumaric, glutamic, lactic, maleic, malic, malonic, mandelic, methanesulfonic, 1,5-naphthalendisulfonic, oxalic, pivalic, propionic, p-toluenesulfonic, succinic, tartaric acids and the like, or any metal salt wherein the metal is selected from sodium, potassium, lithium, calcium, magnesium, zinc, aluminum and the like, or ammonium salts, or any salt formed from organic bases, such as 2-amino-1-butanol, 2-amino-2-ethyl-1,3-propanediol, 2-amino-2-methyl-1,3-propanediol, benzathine, benzyldimethylamine, chloroprocaine, choline, dibenzylmethylamine, diethanolamine, diisopropanolamine, ethylenediamine, dimethyl stearamine, meglumine, 2-methyl-2-amino-1-propanol, monoamine glycols, monoethanolamine, monoisopropanolamine, morpholine, N,N-dibenzylethylenediamine, N,N-dimethyl-2-amino-2-methyl-1-propanol, N,N-dimethylaniline, procaine, pyridine, quinoline, t-butyl-dimethylamine, triethanolamine, triethylamine, trihydroxymethylaminomethane, triisopropanolamine, trimethylamine and the like, and salts with amino acids such as glycine, lysine, arginine, taurine, histidine, alanine, valine, cysteine and the like.

The preferred compounds to be used in the methods of the present invention are shown below:
1-phenylvinyl 4-methoxybenzoate;
1-(4-methoxyphenyl)-vinyl 4-tert-butylbenzoate;
1-(4-tert-butylphenyl)-vinyl 4-methoxybenzoate;
1-phenylvinyl 4-tert-butylbenzoate;
4-benzoyloxy-2-methoxybenzenesulfonic acid;
3-diethylaminophenyl benzoate;
3-(1-pyrrolidinyl)phenyl benzoate;
3-methoxyphenyl benzoate;
phenyl 4-methoxysalicylate; and
3-methoxyphenyl salicylate.

The preferred new compounds of the present invention are shown below:
1-(4-methoxyphenyl)-vinyl 4-tert-butylbenzoate;
1-(4-tert-butylphenyl)-vinyl 4-methoxybenzoate;
1-phenylvinyl 4-tert-butylbenzoate;

4-benzoyloxy-2-methoxybenzenesulfonic acid; and
3-(1-pyrrolidinyl)phenyl benzoate.

Compounds of formula (I) when R is (i) can be obtained by a great variety of methods disclosed in the literature. Schemes 1a-1e illustrate some representative synthetic examples thereof.

Scheme 1a

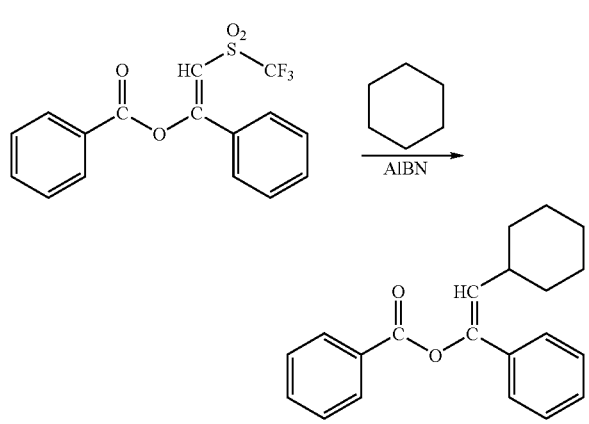

Xiang, J et al., *J. Amer. Chem. Soc.*, 119(18), <1997>, 4123-4129

Scheme 1b

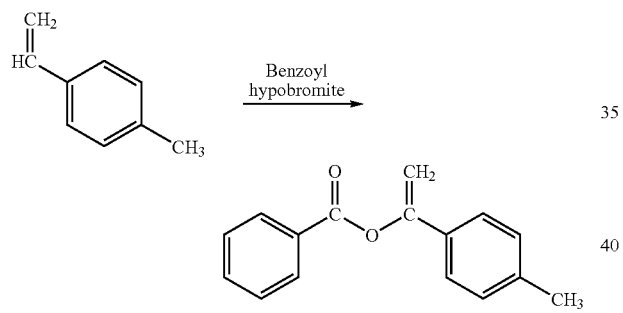

Edwards; Hodges, *J. Chem. Soc.*, <1954>, 761

Scheme 1c

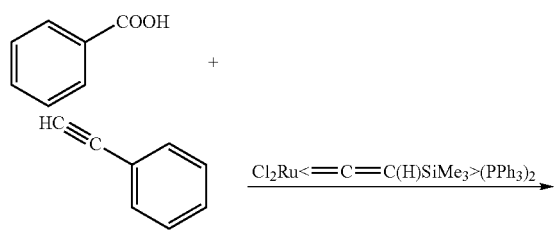

Opstal, T et al., *Syn. Lett.*, <2003>, 314-320

Scheme 1d

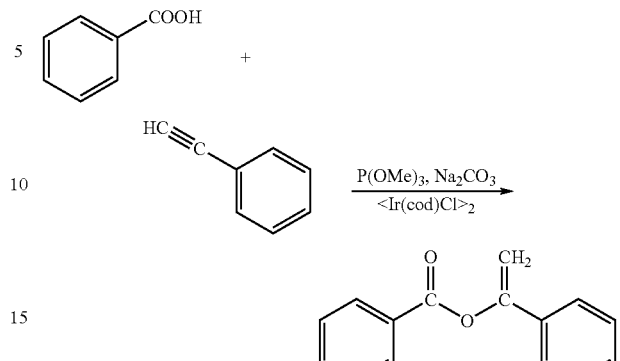

Nakagawa, H et al., *Tetrahedron Lett.*, 44 (1), <2003>, 103-106

Scheme 1e

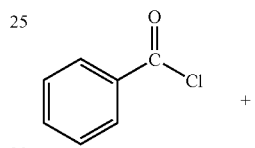

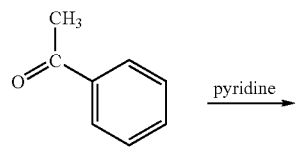

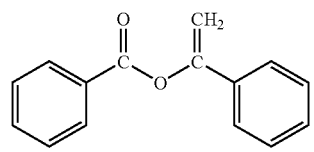

Claisen; Haase, *Chem. Ber.*, 36, <1903>, 3679

Compounds of formula (I) when R is (ii) have not been described yet in the literature, and consequently the present invention relates to said group of compounds per se.

Compounds of formula (I) when R is (iii) are commercially available or can be obtained alternatively by known methods of organic chemistry.

The present invention also relates to a process to prepare the compounds of formula (Ia). When R is (i), the process comprises reacting an acyl halide of formula (II), wherein $R_1$-$R_5$ are as defined above, X is an halogen atom selected from the group consisting of fluorine, chlorine or bromine, preferably chlorine, with a silylenol of formula (III), wherein $R_1$ and $R_6$-$R_{10}$ are as defined above and $R_{19}$-$R_{21}$ are selected independently from $C_1$-$C_6$-alkyl, $C_3$-$C_6$-cycloalkyl and $C_6H_5$—$(CH_2)_r$—, wherein r is 1-4, or two groups can form, together with the silicium atom a ring selected from silolane, sililane and silepane (Scheme 2a)

Scheme 2a

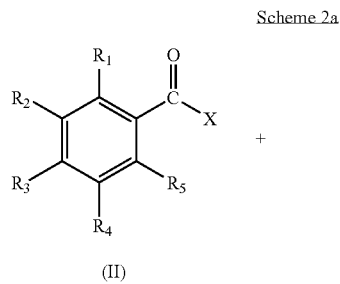

Said reaction occurs conveniently in the presence of a catalyst selected from the group consisting of mercuric chloride, cuprous chloride and mixtures thereof. Optional solvents can be selected from N,N-dimethylformamide, N,N-dimethylacetamide, 1-methyl-2-pyrrolidone, 1-methyl-2-piperidone, 1,3-dimethyl-2-imidazolidinone, and the like, and mixtures thereof. Preferably the solvent is 1,3-dimethyl-2-imidazolidinone.

Intermediate silylenols of formula (III) can be prepared by standard chemical methods. However, some intermediate silylenols of formula (III) have not been described previously in the literature and are included in the present invention. A representative of the new intermediate silylenols is 4-tert-butylacetophenone trimethylsilylenol.

When R is (ii), the process comprises reacting a benzoic acid ester of formula (IV), wherein $R_1$-$R_5$ and $R_{12}$-$R_{14}$ are as defined above, with chlorosulfonic acid followed by an optional esterification reaction with $C_1$-$C_6$-alkyl-OH or $C_3$-$C_6$-cycloalkyl-OH to afford the corresponding $C_1$-$C_6$-alkyl or $C_3$-$C_6$-cycloalkyl sulfonic ester final compounds. Alternatively the process comprises firstly sulfonating a phenol of formula (V) with chlorosulfonic acid followed by esterification with an acid intermediate (VII) wherein $R_1$-$R_5$ are as defined above. Likewise, esterifying the sulfonic acid intermediates (VI) with $C_1$-$C_6$-alkyl-OH or $C_3$-$C_6$-cycloalkyl-OH provides the corresponding $C_1$-$C_6$-alkyl or $C_3$-$C_6$-cycloalkyl sulfonic acid esters thereof, which can be esterified with (VII) to afford the corresponding $C_1$-$C_6$-alkyl or $C_3$-$C_6$-cycloalkyl sulfonic acid ester final compounds (Scheme 2b).

Scheme 2b

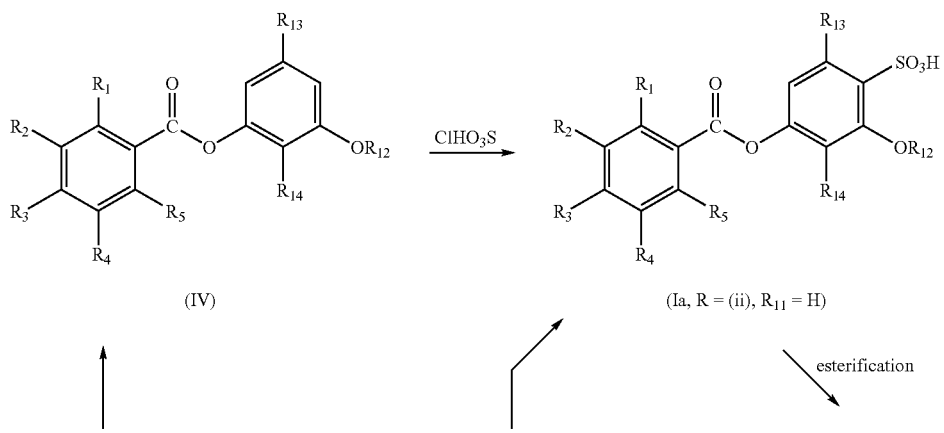

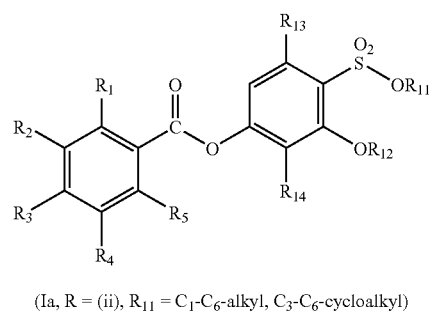

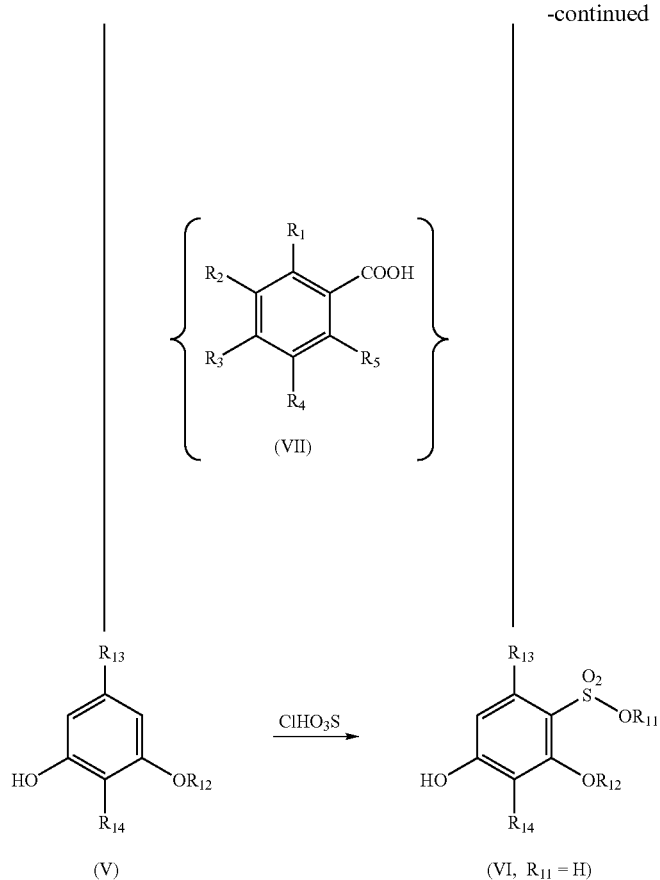

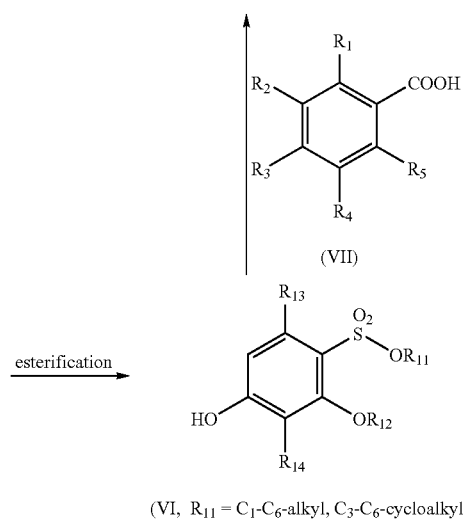

When R is (iii), the process comprises reacting an acyl halide of formula (II), wherein $R_1$-$R_5$ are as defined above, X is an halogen atom selected from the group consisting of fluorine, chlorine or bromine, preferably chlorine, with a phenol of formula (VIII):

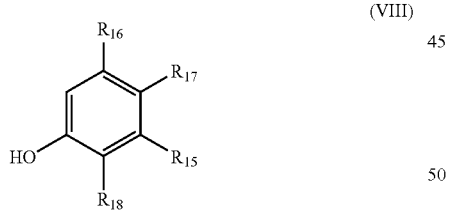

wherein $R_{15}$-$R_{18}$ are as defined above (Scheme 2c)

Scheme 2a

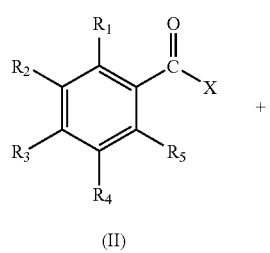

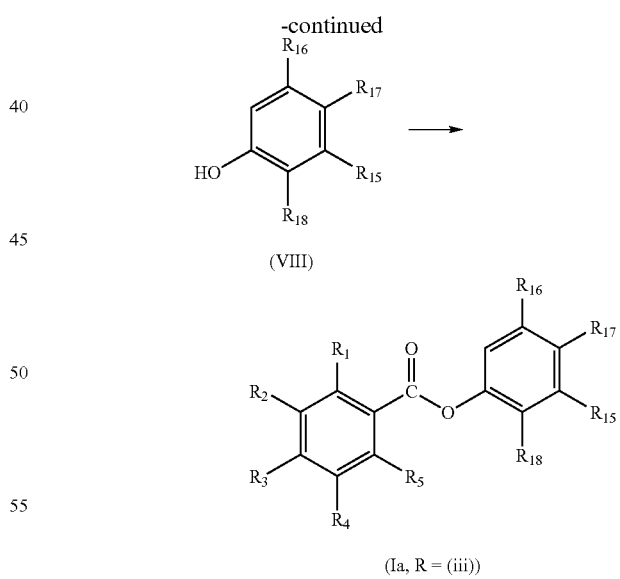

The present invention also relates to the use of benzoic acid ester compounds of formula (I) or salts thereof as photochemical precursors of ultraviolet absorbers.

The present invention also relates to compositions containing at least a benzoic acid ester compound of formula (I) or salts thereof.

The present invention also relates to cosmetic or pharmaceutical compositions comprising an effective amount of at least a benzoic acid ester compound of formula (I) or an acceptable salt thereof susceptible to be photochemically converted in situ to a sunscreen compound with enhanced UV protection ability.

The present invention also relates to a method for protecting a human or animal living body from ultraviolet radiation with a cosmetic or pharmaceutical composition comprising an effective amount of at least a benzoic acid ester compound of formula (I) or an acceptable salt thereof susceptible to be photochemically converted in situ to a sunscreen compound with enhanced UV protection ability.

The present invention also relates to a method for protecting a human or animal living body from ultraviolet radiation with a cosmetic or pharmaceutical composition comprising an effective amount of at least a benzoic acid ester compound of formula (I) or an acceptable salt thereof susceptible to be photochemically converted in situ to a sunscreen compound with enhanced UV protection ability, wherein the human or animal living body is a human being.

Such compositions typically range from 0.01 to 40 wt % based on the total weight of the sunscreen. More typically, the amount falls within the range of 0.05 wt % to 25 wt %. The amount of organic sunscreen compound of formula (I) preferably ranges from about 0.1 wt % to about 15 wt % of the sunscreen formulation.

These sunscreen formulations can contain one or more additional organic sunscreen agents for filtering UVB or UVA rays or they may additionally contain one or more metal oxide sunscreen agents such as titanium dioxide or zinc oxide.

These sunscreen formulations may additionally contain a carrier and at least one component selected from the group consisting of dispersing agents, preservatives, anti-foams, perfumes, fragrances, oils, waxes, propellants, dyes, pigments, emulsifiers, surfactants, thickeners, humectants, exfoliants and emollients. These sunscreen formulations may be in the form of a cosmetic composition with a cosmetically acceptable carrier and one or more cosmetic adjuvants. The sunscreen formulation can optionally have conventional antioxidants or other stabilizers without UV absorbing characteristics.

Other ingredients referred to above and discussed more particularly below are generally used in an amount from about 0.1 wt % to about 10 wt % of the sunscreen formulation. The balance comprises a cosmetically or pharmaceutically acceptable carrier.

Suitable dispersing agents for the sunscreen formulations include those useful for dispersing organic or inorganic sunscreen agents in either a water phase, oil phase, or part of an emulsion, including, for example, chitosan.

Emulsifiers may be used in the sunscreen formulations to disperse one or more of the compounds of formula (I) or other components of the sunscreen formulation. Suitable emulsifiers include conventional agents such as, for example, glycerol stearate, stearyl alcohol, cetyl alcohol, dimethicone copolyol phosphate, hexadecyl-D-glucoside, octadecyl-D-glucoside, etc.

Thickening agents may be used to increase the viscosity of the sunscreen formulations. Suitable thickening agents include carbomers, acrylate/acrylonitrile copolymers, xanthan gum and combinations of these. The carbomer thickeners include the crosslinked acrylic polymers. The amount of thickener within the sunscreen formulation, on a solids basis without water, may range from about 0.001 to about 5%, preferably from 0.01 to about 1% and optimally from about 0.1 to about 0.5% by weight.

Minor optional adjunct ingredients for the sunscreen formulations to be applied to skin or hair may include preservatives, waterproofing agents, fragrances, anti-foam agents, plant extracts (aloe vera, witch hazel, cucumber, etc) opacifiers, skin conditioning agents and colorants, each in amounts effective to accomplish their respective functions.

The sunscreen formulations may optionally contain an ingredient which enhances the waterproof properties such as, compounds that form a polymeric film, such as dimethicone copolyol phosphate, diisostearoyl trimethylolpropane siloxysilicate and dilauroyl trimethylolpropane siloxysilicate, chitosan, dimethicone, polyethylene, polyvinylpyrrolidone (PVP), PVP/vinylacetate, PVP/eiconsene copolymer, adipic acids/diethylene glycol/glycerine crosspolymer and the like. Waterproofing agents may be present at levels of from about 0.01 to about 10% by weight.

The sunscreen formulations may also optionally contain one or more skin conditioning agents. These include humectants, exfoliants and emollients.

Humectants are polyhydric alcohols intended for moisturizing, reducing scaling and stimulating the removal of built scale from the skin. Typically polyhydric alcohols include polyalkylene glycols and more preferably alkylene polyols and their derivatives. Illustrative are propylene glycol, dipropylene glycol, polypropylene glycol, polyethylene glycol, sorbitol, 2-pyrrolidone-5-carboxylate, hydroxypropyl sorbitol, hexylene glycol, ethoxydiglycol 1,3-butylene glycol, 1,2,6-hexanetriol, glycerin, ethoxylated glycerin, propoxylated glycerin and mixtures thereof. Most preferably the humectant is glycerin. Amounts of humectant can range anywhere from 1 to 30%, preferably from 2 to 20% and optimally from about 5 to 10% by weight of the sunscreen composition.

The exfoliants suitable for use in the present invention may be selected from alpha-hydroxy carboxylic acids, beta hydroxycarboxylic acids and salts of these acids. Most preferred are glycolic, lactic and salicylic acids and their alkali, metal or ammonium salts.

Suitable emollients include those agents known for softening the skin or hair which may be selected from hydrocarbons, fatty acids, fatty alcohols and esters. Petrolatum is a common hydrocarbon type of emollient conditioning agent. Other hydrocarbons that may be employed include alkyl benzoates, mineral oils, polyolefins such as polydecene, and paraffins, such as isohexadecane. Fatty acids and alcohols typically have from about 10 to 30 carbon atoms. Illustrative are myristic, isostearic, hydroxystearic, oleic, linoleic, ricinoleic, behenic and eruicic acids and alcohols. Oily ester emollients may be those selected from one or more of the following triglyceride esters, acetoglyceride esters, ethoxylated glycerides, alkyl esters of fatty acids, ether esters, polyhydric alcohol esters and wax esters. Additional emollients or hydrophobic agents include $C_{12}$ to $C_{15}$ alkyl benzoates, dioctyladipate, octyl stearate, octyldodecanol, hexyl laurate, octyldodecyl neopentanoate, cyclomethicone, dicapryl ether, dimethicone, phenyl trimethicone, isopropyl myristate, caprylic/capric glycerides, propylene glycol dicaprylate/dicaprate and decyl oleate.

The sunscreen formulations may optionally contain one or more inorganic sunscreen agents as discussed above including micro fine surface treated titanium dioxide and micro fine untreated and surface treated zinc oxide. Titanium dioxide in the sunscreen compositions preferably has a mean primary particle size of between 5 and 150 nm and preferably from 10 to 100 nm. The zinc oxide in the sunscreen compositions preferably has a mean primary particle size of between 5 nm and 150 nm, preferably between 10 nm and 100 nm.

The sunscreen compositions may also contain one or more additional monomeric organic chromophoric compounds. These can either be UVA, UVB or broad band filters.

Examples of suitable UVA sunscreens include benzophenone derivatives, menthyl anthranilate, butyl methoxydibenzoyl methane and benzylidene-dioxoimidazoline derivatives. Examples of suitable UVB sunscreens include cinnamate derivatives, salicylate derivatives, p-aminobenzoic acid derivatives, camphor derivatives, phenylbenzimidazole derivatives and diphenylacrylate derivatives. Examples of suitable broad-band sunscreen include benzotriazole derivatives and triazine derivatives such as anisotriazone. Others include ethylhexyltriazone and diethylhexylbutamidotriazone. Particularly useful organic sunscreen agents that can be introduced are avobenzone, 2-ethylhexyl p-methoxycinnamate, oxybenzone, octyldimethyl p-aminobenzoic acid, dioxybenzone, ethyl-4-[bis(hydroxypropyl)]aminobenzoate, 2-ethylhexyl-2-cyano-3,3-diphenylacrylate, 2-ethylhexylsalicylate, glycerol p-aminobenzoate, 3,3,5-trimethylcyclohexylsalicylate, methylanthranilate, p-dimethylaminobenzoic acid, 2-ethylhexyl p-dimethylaminobenzoate, 2-phenylbenzimidazole-5-sulfonic acid, 2-p-dimethylaminophenyl-5-sulfoniobenzoxazoic acid, sulisobenzone, and mixtures thereof. Examples of useful commercially available organic sunscreen agents that can be introduced include 2-phenylbenzimidazole-5-sulphonic acid, 2-(4-methylbenzylidene)-camphor and 4-isopropyldibenzoylmethane. Although not preferred, the sunscreen formulation may contain an additional antioxidant. Examples of suitable antioxidants which provide stability include p-hydroxybenzoic acid and its esters, salicylates, cumarin derivatives, flavones, hydroxy or methoxy substituted benzophenones, uric or tannic acid and its derivatives, hydroquinone, and benzophenones.

In addition to providing sunscreen activity at levels which provide UV absorption, the compounds of formula (I) can be introduced into a skin care formulation, a hair care formulation or other personal care formulations such as cosmetic or pharmaceutical compositions at levels which provide antioxidant activity. These compounds can be used with or without conventional antioxidants in personal care formulations such as hair care, skin care and cosmetic and pharmaceutical compositions.

In the cosmetics field, and in particular for make-up compositions such as foundation compositions, tinted creams, mascaras, blushers and eye shadows, lipsticks and nail varnishes, pigments are being sought which are capable of imparting to these various types of products a varied palette of colorations which are reproducible over time and are insoluble in most of the cosmetic media used such as water and cosmetically acceptable solvents. These pigments should, moreover, be stable at the pHs usually used or encountered in the cosmetics field.

Cosmetic or pharmaceutical products, such as skin lotions, collagen creams, sunscreen, facial make-up, etc., comprise synthetic materials such as antifoams, antioxidants, antiperspirants, colorants, dyes, emollients, emulsifiers, exfoliants, humectants, lipids, moisturizers, perfumes, fragrances, pigments, preservatives, propellants, skin conditioners, solvents, surfactants, thickeners, water proofing agents, etc.; as well as natural products such as collagen, proteins, mink oil, olive oil, coconut oil, carnauba wax, beeswax, lanolin, cocoa butter, xanthan gum, aloe, etc.

The present invention also relates to a method to improve the photostability of a sunscreen formulation that comprises adding at least a benzoic acid ester compound of formula (I) or an acceptable salt thereof to said sunscreen composition in an amount sufficient to improve the photostability of said sunscreen agent.

The present invention also relates to a personal care composition which comprises at least a benzoic acid ester compound of formula (I) or an acceptable salt thereof in an amount effective to photostabilize composition ingredients from sun radiation.

The cosmetic, pharmaceutical and personal care compositions can be in the form of creams, ointments, milks, suspensions, powders, oils, lotions, gels, sticks, foams, emulsions, dispersions, sprays and aerosols, and the like. More specific forms include lipsticks, foundations, makeup, loose or press powders, eye blushes, eye shadows, mascaras, nail varnishes, nail lacquers and non permanent dyeing compositions for the hair, and the like.

The present invention also relates to industrial compositions comprising an effective amount of at least a benzoic acid ester compound of formula (I) or an acceptable salt thereof susceptible to be photochemically converted in situ to a sunscreen compound with enhanced UV protection ability.

The present invention also relates to a method for protecting a material from ultraviolet radiation comprising treating said material by an industrial composition comprising an effective amount of at least a benzoic acid ester compound of formula (I) or an acceptable salt thereof susceptible to be photochemically converted in situ to a sunscreen compound with enhanced UV protection ability, wherein said material is selected from the group consisting of organic compounds, oils, fats, waxes, gelatins, sunscreens, polymers, such as polyolefins, polyketones, polystyrene, polyvinyl chloride (PVC), polyacrylates, polymethacrylates, polyacrylamides, polyacrylonitriles, polyvinyl alcohol derivatives, polyvinyl acetate derivatives, polyurethanes, polyamides, polyesters, polyureas, polycarbonates, polysiloxanes, polyketimines, radiation curable compositions, resins, such as hydrocarbon resins, phenol/formaldehyde resins, urea/formaldehyde resins, melamine/formaldehyde resins, unsaturated polyester resins, crosslinkable acrylic resins, crosslinked epoxy resins, epoxy/melamine resins, varnishes, cellulose, cellulose-based paper formulations, photographic materials, photographic film paper, metallic products, ceramic products, biocides, natural textile fibers, textile fabrics, dyes, inks, pigments, paints, coatings, adhesives, leathers, woods, rubbers, glasses, lenses, composites, mixtures or blends thereof, and the like.

The compounds of the present invention are particularly useful as ultraviolet light absorber agents for stabilizing a wide variety of materials including, for example, naturally occurring and synthetic organic compounds, oils, fats, waxes, sunscreens, organic dyes and biocides, and particularly various organic artificial polymers used in applications such as photographic materials, photographic film paper, plastics, artificial textile fibers such as polyamide and polyester, polyurethane, natural textile fibers such as silk, cotton and wool, natural or synthetic rubbers, paints and other coatings, adhesives, resins, natural fibers and laminated UV screening window films, natural polymers such as cellulose and cellulose-base paper formulations, rubber, gelatin and chemically modified homologous derivatives, inks, polysiloxanes, metallic products, wood products, ceramic products, lenses, composites, mixtures or blends thereof, and the like, among others.

Cellulose-based paper formulations uses comprise newsprint, cardboard, posters, packaging, labels, stationery, book and magazine paper, bond typing paper, multi-purpose and office paper, computer paper, xerographic paper, laser and ink-jet printer paper, offset paper, currency paper, and the like.

The compounds of the present invention may also be employed to form light stabilizing compositions. Such light stabilizing compositions may include a variety of other components known in the art including triazines, benzotriazoles, hindered amine light stabilizers, radical scavengers, antioxidants and the like.

The present invention also relates to the use of compounds of formula (I) to prepare cosmetic or pharmaceutical compositions, personal care compositions and industrial compositions that, upon phototransformation, indicate the amount of UVB radiation received.

Polymers which can be stabilized include naturally occurring and synthetic organic materials which may be mixtures of compounds, including mineral oils, animal and vegetable fats, oils and waxes, or oils, fats or waxes based on synthetic esters (e.g., phthalates, adipates, phosphates or trimellitates) and also mixtures of synthetic esters with mineral oils in any ratio.

The compounds of the present invention are typically employed in amounts from about 0.01 to about 30% by weight, preferably from about 0.05 to about 20% by weight, and most preferably from about 0.1 to about 10% by weight, based on the weight of the material to be stabilized.

The compounds of the present invention can be incorporated into such materials in any one of a variety of conventional procedures, including for example, physical mixing or blending, optionally, with chemical bonding to the material (typically to a polymer), as a component in a light stabilizing or oxidation composition such as a coating or solution, or as a component in a UV screening composition such as a sunscreen composition.

Natural or synthetic rubbers such as natural latex or lattices of carboxylated styrene/butadiene copolymers may be formulated as aqueous emulsions.

Organic dyes encompass azo dyes (diazo, triazo and polyazo), anthraquinones, benzodifuranones, polycyclic aromatic carbonyl dyes, indigoid dyes, polymethines, styryl dyes, di- and triaryl carbonium dyes, phthalocyanines, quinophthalones, sulfur dyes, nitro and nitroso dyes, stilbene dyes, formazan dyes, quinacridones, carbazoles and perylene tetracarboxylic diimides.

When compositions are used in the form of emulsions, they may additionally contain surface-active agents which are well known in the state of the art, such as anionic, nonionic, cationic or amphoteric surface-active agents or mixtures thereof.

These compositions may also contain fatty substances, organic solvents, silicones, thickening agents, softening agents, surfactants, sunscreen agents, anti-free-radical agents, anti-foaming agents, moisturizing agents, fragrances, preserving agents, antioxidants, fillers, sequestering agents, treatment agents such as nonionic, cationic, anionic or amphoteric polymers or mixtures thereof, propellants, and basifying or acidifying agents, or other pigments.

The fatty substances may consist of an oil or a wax or mixtures thereof, fatty acids, fatty alcohols, fatty acid esters, vaseline, paraffin, lanolin, hydrogenated lanolin or acetylated lanolin.

The oils are chosen from animal oils, vegetable oils, mineral oils or synthetic oils and especially hydrogenated palm oil, hydrogenated castor oil, liquid paraffin, paraffin oil, purcellin oil and silicone oils.

The waxes are chosen from animal waxes, fossil waxes, vegetable waxes, mineral waxes or synthetic waxes. Beeswaxes, carnauba wax, candelilla wax, sugar cane wax, Japan wax, ozokerites, montan wax, microcrystalline waxes and paraffin waxes may more particularly be mentioned.

The sunscreen activity of the benzoic acid ester compounds of the present invention is based on efficient phototransposition reactions showing a high chemical yield.

The phototransposition of compounds of formula (I) when R is (i) provides dibenzoylmethane compounds of formula (IX), according to Scheme 3.

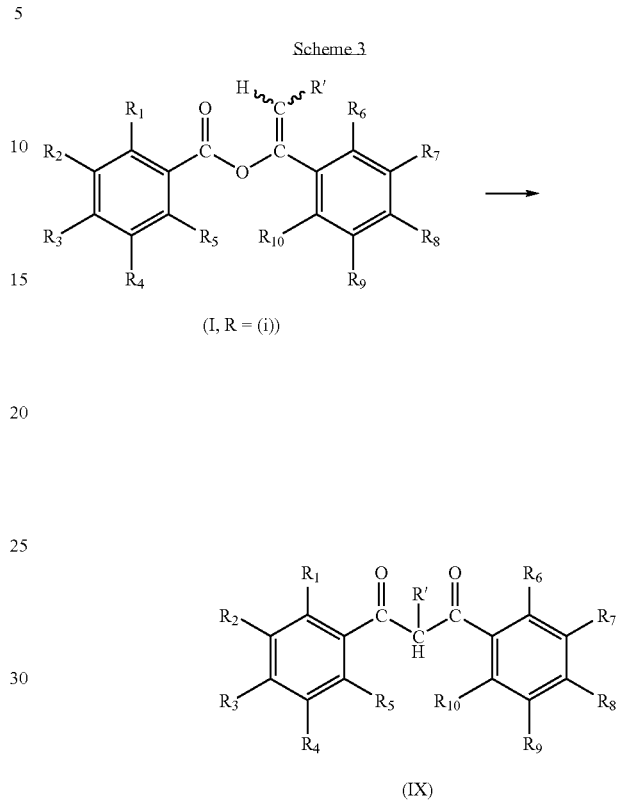

Such dibenzoylmethane compounds constitute a recognized chemical sunscreen series, being avobenzone the most representative. Thus, phototransposition of both 1-(4-methoxyphenyl)-vinyl 4-tert-butylbenzoate and 1-(4-tert-butylphenyl)-vinyl 4-methoxybenzoate yields the authorized and widely used avobenzone sunscreen compound.

The photo-Fries transposition of compounds of formula (I) wherein R is (ii) or (iii) provides benzophenone compounds of formula (X), according to Scheme 4:

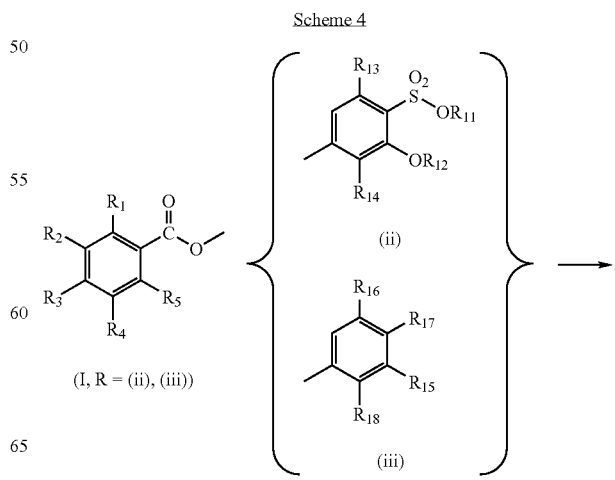

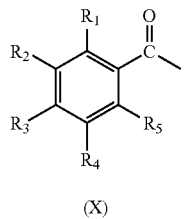

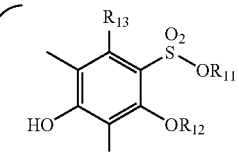

(ii)

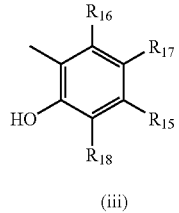

(iii)

Such benzophenone compounds constitute a recognized and widely used chemical sunscreen series. Dioxybenzone, oxybenzone and sulisobenzone are the most representative compounds in said series. Phototransposition of both 3-methoxyphenylsalicylate and phenyl 4-methoxysalicylate provides dioxybenzone. Phototransposition of 3-methoxyphenyl benzoate leads to oxybenzone. And phototransposition of 4-benzoyloxy-2-methoxybenzenesulfonic acid leads to sulisobenzone.

The photo-Fries transposition of compounds of formula (I) wherein $R_{15}$ is a dialkylamino group provides a recent sunscreen benzophenone series, being 4-diethylamino-2-hydroxybenzophenone and 2-hydroxy-4-(1-pyrrolidinyl)benzophenone the most representative compounds in said series. Phototransposition of 3-diethylaminophenyl benzoate and 3-(1-pyrrolidinyl)phenyl benzoate provides 4-diethylamino-2-hydroxybenzophenone and 2-hydroxy-4-(1-pyrrolidinyl) benzophenone respectively.

The compounds of formula (I) show a progressive UV protection depending on the time to sun exposition and the degree of sun radiation. This progressive UV protection property is evidenced in their UVB and particularly UVA screening ability. Consequently, the compositions containing compounds of formula (I) constitute a safer method to take sunbaths and produce a more uniform and glamorous tanning than conventional sunscreens. Moreover the compounds resulting from the phototranspositions belong to recognized chemical sunscreen series which ensure the convenience of the method.

Accordingly, the present invention also relates to the use of compounds of formula (I) to prepare cosmetic or pharmaceutical compositions, personal care compositions and industrial compositions characterized by a progressive UV protection depending on the time to sun exposition and the degree of sun radiation.

The following non-limiting examples illustrate the scope of the present invention.

Preparation Example 1

4-Methoxyacetophenone trimethyl-silylenol

A solution of 0.82 g (5.5 mmol) of 4-methoxyacetophenone in 3.4 mL of tetrahydrofuran was added to 7 mmol of lithium diisopropylamine (LDA) generated in situ. After stirring the solution for 30 minutes, 4.5 mL of trimethylsilyl chloride were added and the mixture was stirred for 17 h at room temperature under nitrogen atmosphere. Then pentane was added, the mixture was filtered to remove the lithium salts and the solvent was evaporated to dryness under reduced pressure. The obtained crude contained 78% ($^1$H-NMR) of 4-methoxyacetophenone trimethylsilylenol.

$^1$H-NMR: 3.78 (s, 3H), 4.32 (d, 1H, J=2 Hz), 4.79 (d, 1H, J=2 Hz), 6.85 (d, 2H, J=9 Hz), 7.52 (d, 2H, J=9 Hz)

Preparation of LDA: Under nitrogen atmosphere, 0.97 mL of distilled diisopropylamine were dissolved in 7 mL of anhydrous tetrahydrofuran at 0° C. Then 4.4 mL of butyl lithium 1.6M in hexane were added and the mixture was stirred for 20 minutes.

Preparation Example 2

4-Tert-butylacetophenone trimethylsilylenol

A solution of 1.25 mL (6.7 mmol) of 4-tert-butylacetophenone in 4 mL of tetrahydrofuran was added to LDA (7 mmol) generated in situ. After stirring the solution for 30 minutes, 4.5 mL of trimethylsilyl chloride were added and the mixture was stirred for 16 h at room temperature under nitrogen atmosphere. Then pentane was added, the mixture was filtered to remove the lithium salts and the solvent was evaporated to dryness under reduced pressure. The obtained crude contained 100% ($^1$H-NMR) of 4-tert-butylacetophenone trimethylsilylenol.

$^1$H-NMR: 1.32 (s, 9H), 4.38 (d, 1H, J=2 Hz), 4.87 (d, 1H, J=2 Hz), 7.34 (d, 2H, J=9 Hz), 7.52 (d, 2H, J=9 Hz)

Preparation Example 3

1-Phenylvinyl 4-tert-butyl-benzoate

A mixture of 4.16 g (21.62 mmol) of acetophenone trimethylsilylenol, 4.33 g (22.01 mmol) of 4-tert-butylbenzoyl chloride and 136 mg of mercuric chloride was heated at 100° C. for 2 h. The mixture was then left to cool, water was added over the reaction crude and extracted with dichloromethane. The organic phase was dried over magnesium sulfate and the solvent was removed under reduced pressure. A 2.12 g sample was purified by flash chromatography (hexane: dichloromethane 3:1) giving 1.17 g of 1-phenylvinyl 4-tert-butylbenzoate. Yield 57%.

$^1$H-NMR: 1.36 (s, 9H), 5.14 (d, 1H, J=2 Hz), 5.58 (d, 1H, J=2 Hz), 7.32 (m, 3H), 7.53 (m, 2H), 8.13 (dt, 2H, J=9 Hz, 2 Hz).

$^{13}$C-NMR: 164.63/s —CO—, 157.23/s —C═CH$_2$, 153.03/s —C═C—(CH$_3$)$_3$, 134.28/s —C—C═CH$_2$, 129.94/d 2 CH aromatic, 128.81/d 1 CH aromatic, 128.41/d 2 CH aromatic, 126.55/s —C—CO—, 125.50/d 2 CH aromatic, 124.81/d 2 CH aromatic, 102.14/t CH$_2$, 35.26/s —C—(CH$_3$)$_3$, 31.18/q 3 CH$_3$.

IR: 1737, 1642, 1607, 1249 cm$^{-1}$.

Preparation Example 4

1-Phenylvinyl 4-methoxybenzoate

A mixture of 2.38 g (12.37 mmol) of acetophenone trimethylsilylenol, 2.15 g (12.60 mmol) of 4-methoxybenzoyl chloride and 93 mg of mercuric chloride was heated at 100° C. for 2 h. The mixture was then left to cool to room temperature, and then water was added over the reaction crude, and extracted with dichloromethane. The organic phase was dried over magnesium sulfate and the solvent was removed under reduced pressure. The obtained crude contained 75-85% of 1-phenylvinyl 4-methoxybenzoate as determined by $^1$H-NMR.

Preparation Example 5

1-(4-Methoxyphenyl)-vinyl 4-tert-butylbenzoate 4-tert-butylbenzoyl chloride (1.78 g, 9 mmol), 0.47 g of cuprous chloride and 4 mL of 1,3-dimethyl-2-imidazolidinone were added to crude 4-methoxyacetophenone trimethylsilylenol (4.3 mmol). After stirring the solution for 21 hours at room temperature, 1 mL of triethylamine and 10 mL of chloroform were added. Then the solution was chromatographied through flash silica column (hexane/ethyl acetate 10:1). The first collected fraction was purified by flash chromatography (hexane/dichloromethane 3:2) giving 0.34 g of 1-(4-methoxyphenyl)-vinyl 4-tert-butylbenzoate. Yield 25%.

$^1$H-NMR: 1.37 (s, 9H), 3.80 (s, 3H), 5.03 (d, 1H, J=2 Hz), 5.46 (d, 1H, J=2 Hz), 6.85 (dt, 2H, J=2 Hz, 9 Hz), 7.46 (dt, 2H, J=2 Hz, 9 Hz), 7.52 (dt, 2H, J=2 Hz, 9 Hz), 8.12 (dt, 2H, J=2 Hz, 9 Hz).

$^{13}$C-NMR: 164.69/s —CO—, 159.99/s —C—OCH$_3$, 157.18/s —C═CH$_2$, 152.83/s —C—C—(CH$_3$)$_3$, 129.93/d 2 CH aromatic, 126.94/s 1 CH aromatic, 126.63/s 1 CH aromatic, 126.25/d 2 CH aromatic, 125.50/d 2 CH aromatic, 113.84/d 2 CH aromatic, 100.27/t CH$_2$, 55.33/q CH$_3$—O, 35.26/s —C—(CH$_3$)$_3$, 31.18/q 3 CH$_3$.

IR: 1735, 1608, 1512, 1245, 1176, 1095 cm$^1$.

Mp: 87-89° C.

Preparation Example 6

1-(4-Tert-butylphenyl)-vinyl 4-methoxybenzoate 4-methoxybenzoyl chloride (2.35 g, 13.8 mmol), 0.65 g of cuprous chloride and 5.6 mL of 1,3-dimethyl-2-imidazolidinone were added to crude 4-tert-butylacetophenone trimethylsilylenol (6.7 mmol). After stirring the solution for 20 hours at room temperature, 1.4 mL of triethylamine and 10 mL of chloroform were added. Then the solution was chromatographied through flash silica column (hexane/ethyl acetate 10:1). The first collected fraction was purified twice by flash chromatography (hexane/dichloromethane 3:2 and next, hexane/dichloromethane 4:1) giving 0.14 g of an uncolored oil corresponding to 1-(4-tert-butylphenyl)-vinyl 4-methoxybenzoate. Yield 7%.

$^1$H-NMR: 1.29 (s, 9H), 3.86 (s, 3H), 5.09 (d, 1H, J=2 Hz), 5.53 (d, 1H, J=2 Hz), 6.97 (2H), 7.35 (dt, 2H, J=2 Hz, 9 Hz), 7.46 (dt, 2H, J=2 Hz, 9 Hz), 8.15 (dt, 2H, J=2 Hz, 9 Hz).

$^{13}$C-NMR: 164.37/s —CO—, 163.63/s —C—OCH$_3$, 153.01/s —C═CH$_2$, 151.80/s —C—C—(CH$_3$)$_3$, 132.06/d 2 CH aromatic, 131.42/s —C—C═CH$_2$, 125.32/d 2 CH aromatic, 124.48/d 2 CH aromatic, 121.67/s C—CO, 113.72/d 2 CH aromatic, 101.29/t CH$_2$, 55.44/q CH$_3$—O, 34.62/s —C—(CH$_3$)$_3$, 31.21/q 3 CH$_3$.

IR: 1732, 1606, 1510, 1246, 1167, 1090 cm$^{-1}$.

Preparation Example 7

4-Benzoyloxy-2-methoxybenzene-sulfonic acid

A solution of 0.47 mL (7.01 mmol) of chlorosulfonic acid in 7 mL of dichloromethane was added drop by drop to a solution of 1.6 g (7.01 mmol) of 3-methoxyphenyl benzoate in 12 mL of dichloromethane at 0° C. Once the addition was completed, the mixture was left to react for 18 h at room temperature. The formed precipitate was filtered, giving 300 mg of 4-benzoyloxy-2-methoxybenzenesulfonic acid. Yield 15%.

$^1$H-NMR: 3.76 (s, 3H), 6.77 (dd, 1H, J=2 Hz, 8 Hz), 6.94 (d, 1H, J=2 Hz), 7.62 (m, 2H), 7.76 (m, 2H), 8.15 (m, 2H).

$^{13}$C-NMR: 164.23/s CO, 156.84/s C—OCH$_3$, 151.87/s C—OCOPh, 133.89/d 1 CH aromatic, 133.21/s C—COO, 129.64/d 2 CH aromatic, 128.89/d 1 CH aromatic, 128.81/d 2 CH aromatic, 128.73/s C—SO$_3$H, 112.03/d 1 CH aromatic, 106.04/d 1 CH aromatic, 55.84/d CH$_3$.

IR: 3500, 1727, 1264, 1198 cm$^{-1}$.

Preparation Example 8

3-Diethylaminophenyl benzoate

A mixture of 1.53 g (9.3 mmol) of 3-diethylaminophenol, 1.35 mL (11.8 mmol) of benzoyl chloride and 1 mL of pyridine in 50 mL of toluene was refluxed for 3 hours. The mixture was then left to cool and the solvent was removed by distillation under reduced pressure. The obtained crude was purified by flash chromatography (hexane/ethyl acetate 7:1) providing a red oil fraction (235 mg) containing mainly 3-diethylaminophenyl benzoate.

Preparation Example 9

3-Methoxyphenyl benzoate

Phosphorus oxychloride (3.16 mL) was added over a mixture of 2.95 g (24.16 mmol) of benzoic acid and 3 g (24.16 mmol) of 3-methoxyphenol, and the resulting mixture was heated at 125° C. for 45 minutes under argon atmosphere. The mixture was cooled to room temperature, water was added over the reaction crude and extracted with diethyl ether. The organic phase was dried over magnesium sulfate and the solvent was removed under reduced pressure yielding 5.0 g of a dark red oil. The obtained crude was purified by flash chromatography (hexane/ethyl acetate 10:1) to afford 2.10 g of 3-methoxyphenyl benzoate. Yield 38%.

Preparation Example 10

Phenyl 4-methoxysalicylate

Phosphorus oxychloride (2 mL) was added over a mixture of 2.00 g (11.89 mmol) of 4-methoxysalicylic acid and 2.13 g (22.65 mmol) of phenol, and the resulting mixture was heated at 115° C. for 15 minutes under argon atmosphere. The mixture was cooled to room temperature, water was added over the reaction crude and extracted with dichloromethane. The organic phase was dried over magnesium sulfate and the solvent was removed under reduced pressure yielding 4.5 g of a dark red oil. The obtained crude was purified by flash chromatography (hexane/ethyl acetate 8.5:1) to afford 1.97 g of phenyl 4-methoxysalicylate. Yield 65%.

Preparation Example 11

3-Methoxyphenyl salicylate

Phosphorus oxychloride (2 mL) was added over a mixture of 2.00 g (14.48 mmol) of salicylic acid and 3.3 mL (28.96 mmol) of 3-methoxyphenol, and the resulting mixture was heated at 115° C. for 15 minutes under argon atmosphere. The mixture was cooled to room temperature, water was added over the reaction crude and extracted with dichloromethane.

The organic phase was dried over magnesium sulfate and the solvent was removed under reduced pressure yielding 4.0 g of a black oil. The obtained crude was purified by flash chromatography (hexane/ethyl acetate 9:1) to afford 2.36 g of 3-methoxyphenyl salicylate. Yield 85%.

Preparation Example 12

3-(1-pyrrolidinyl)phenyl benzoate

A mixture of 1.52 g (9.3 mmol) of 3-(1-pyrrolidinyl)phenol, 1.35 mL (11.8 mmol) of benzoyl chloride and 1 mL of pyridine in 50 mL of toluene was refluxed for 3 hours. The mixture was then left to cool and the solvent was removed by distillation under reduced pressure. The obtained crude was purified by flash chromatography (hexane/ethyl acetate 7:1) providing a red oil fraction (233 mg) containing mainly 3-(1-pyrrolidinyl)phenyl benzoate.

Phototransposition Example 1

Phototransposition of 1-phenylvinyl 4-methoxybenzoate

A solution of 5 mg of 1-phenylvinyl 4-methoxybenzoate in 10 mL of methanol was irradiated with UVB lamps (60 W·m$^2$) for 20 minutes at 35° C. The crude reaction spectrum showed a new absorption band in UVA zone due to dibenzoylmethane fragment. The conversion to benzoyl-4-methoxybenzoyl-methane was observed from the beginning, being the complete conversion in 5 minutes. The phototransposition kinetics is shown in FIG. 1.

Phototransposition Example 2

Phototransposition of 1-(4-methoxyphenyl)-vinyl 4-tert-butylbenzoate

Figure 2:
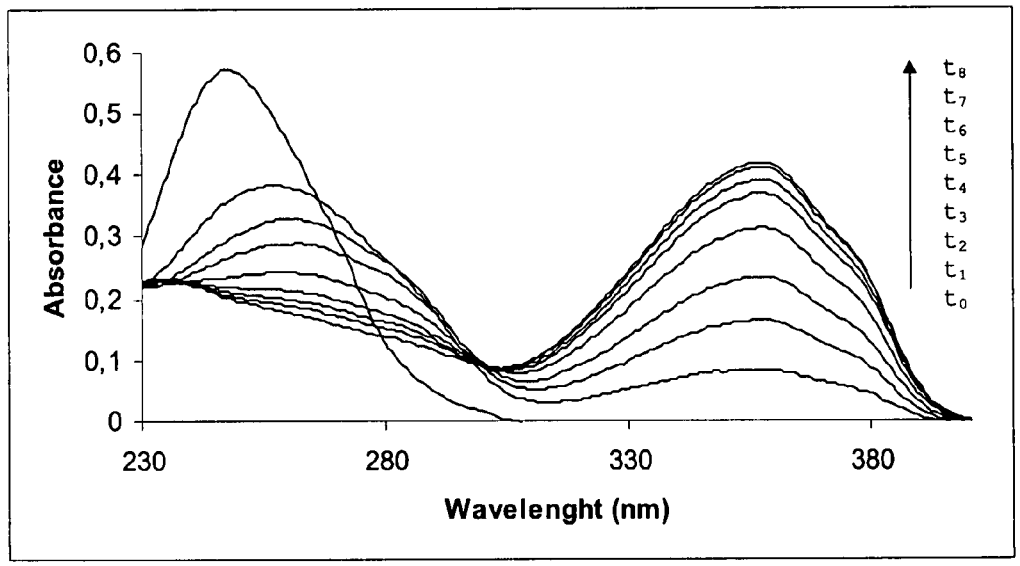
FIG. 2 shows the phototransposition kinetics of 1-(4-methoxyphenyl)-vinyl 4-tert-butylbenzoate.
Figure 2:
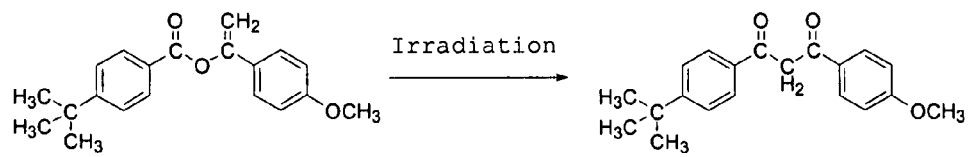

A sample of 4 mL of a solution containing 0.231 mg of 1-(4-methoxyphenyl)-vinyl 4-tert-butylbenzoate in 50 mL of methanol was irradiated with UVB lamps (60 W·m$^{-2}$) for 10 minutes at 35° C. The conversion to avobenzone was completed in 5 minutes. The phototransposition kinetics is shown in FIG. 2.

Phototransposition Example 3

Phototransposition of 1-(4-tert-butylphenyl)-vinyl 4-methoxybenzoate

Figure 3:
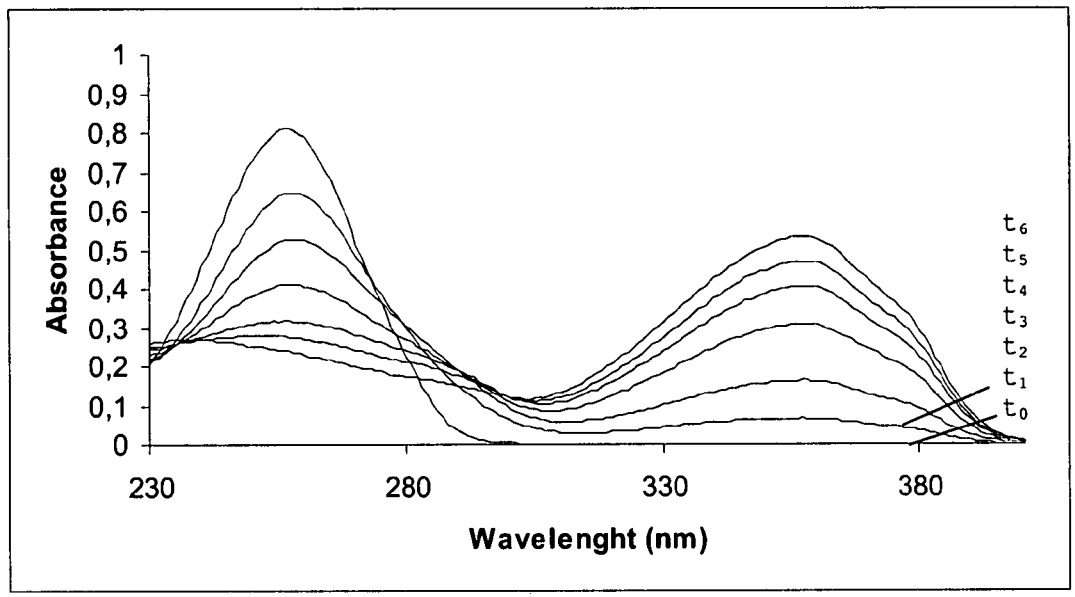
FIG. 3 shows the phototransposition kinetics of 1-(4-tert-butylphenyl)-vinyl 4-methoxybenzoate.
Figure 3:
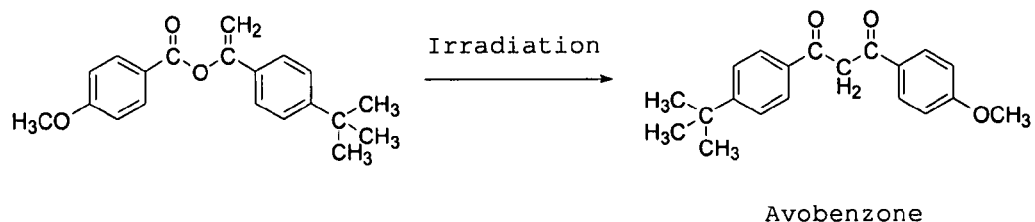

A sample of 4 mL of a solution containing 0.400 mg of 1-(4-tert-butylphenyl)-vinyl 4-methoxybenzoate in 50 mL of methanol was irradiated with UVB lamps (60 W·m$^{-2}$) for 10 minutes at 35° C. The conversion to avobenzone was completed in 5 minutes. The phototransposition kinetics is shown in FIG. 3.

Phototransposition Example 4

Phototransposition of 4-benzoyloxy-2-methoxybenzenesulfonic acid

Figure 4:
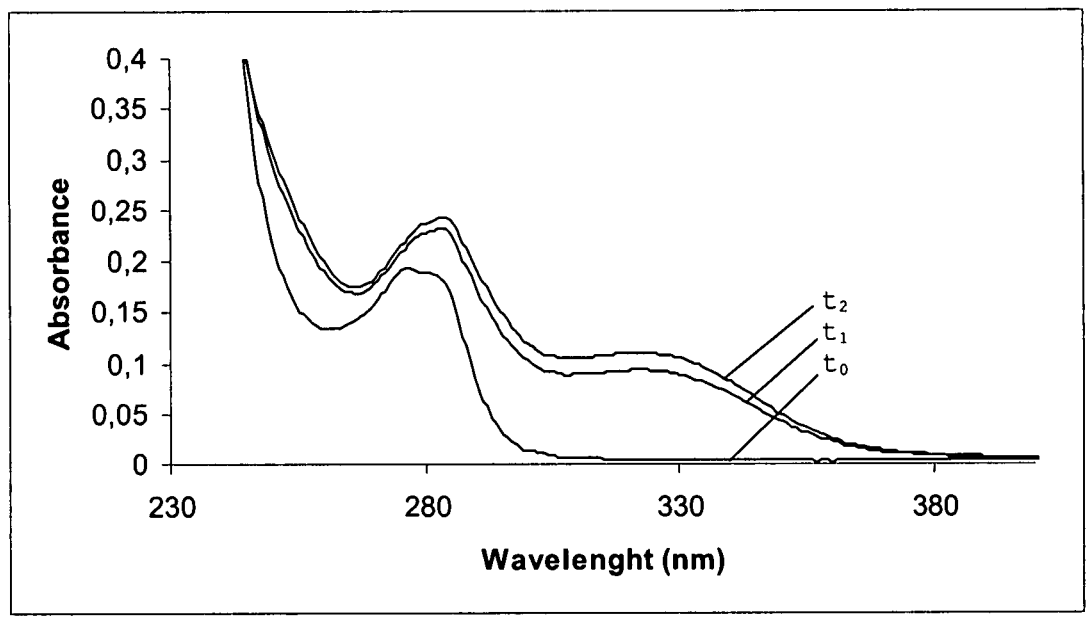
FIG. 4 shows the phototransposition kinetics of 4-benzoyloxy-2-methoxybenzenesulfonic acid.
Figure 4:
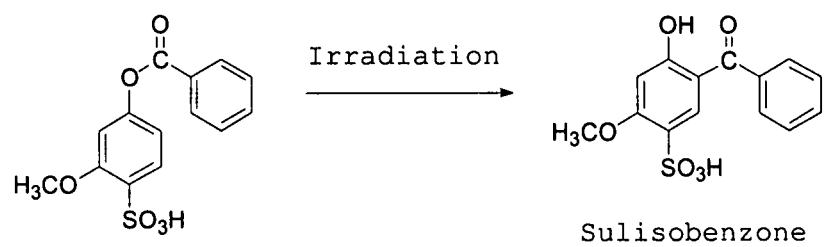

A solution containing 5 mg of 4-benzoyloxy-2-methoxybenzenesulfonic acid in 10 mL of methanol was irradiated with UVB lamps (60 W·m$^{-2}$) for 20 minutes at 35° C. The absorption spectrum was then recorded minute by minute. The conversion to sulisobenzone was complete in 10 minutes. The phototransposition kinetics is shown in FIG. 4.

Phototransposition Example 5

Phototransposition of 3-diethylaminophenyl benzoate

Figure 5:
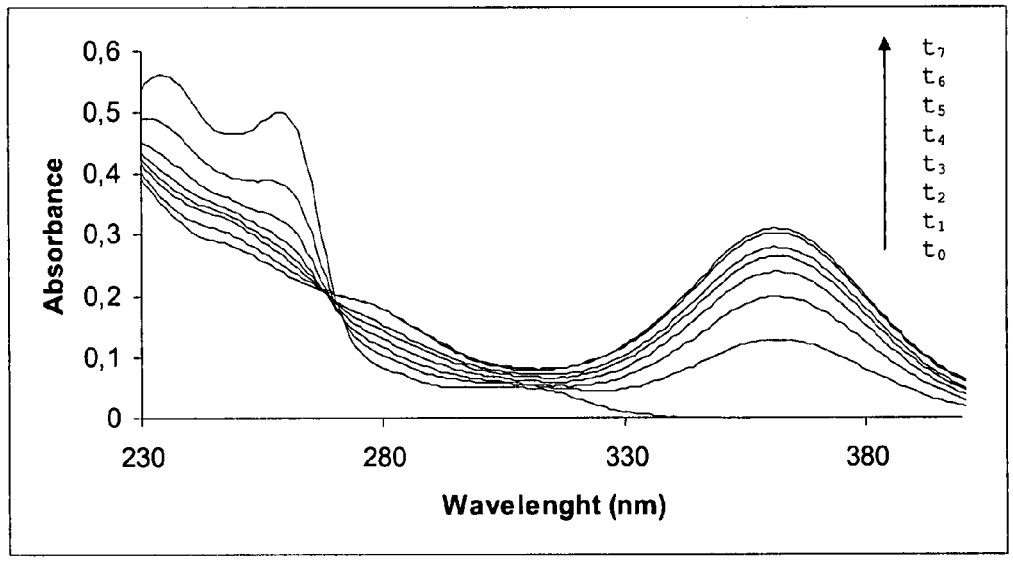
FIG. 5 shows the phototransposition kinetics of 3-diethylaminophenyl benzoate.
Figure 5:
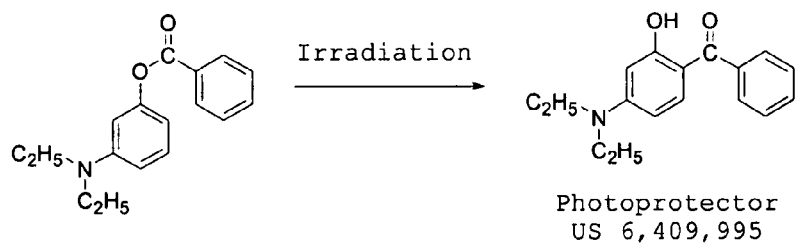

A sample of 4 mL of a solution containing 0.395 mg of 3-diethylaminophenyl benzoate in 50 mL of methanol was irradiated with UVB lamps (60 W·m$^{-2}$) for 20 minutes at 35° C. The phototransformation to 4-diethylamino-2-hydroxybenzophenone was completed in 10 minutes. The phototransposition kinetics is shown in FIG. 5.

Phototransposition Example 6

Phototransposition of 3-methoxyphenyl benzoate

Figure 6:
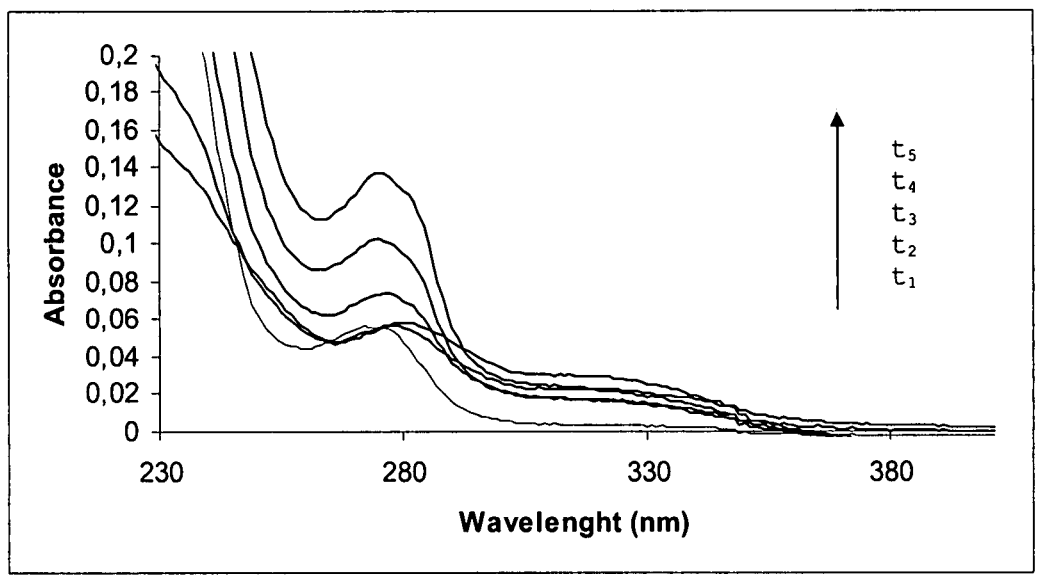
FIG. 6 shows the phototransposition kinetics of 3-methoxyphenyl benzoate.
Figure 6:
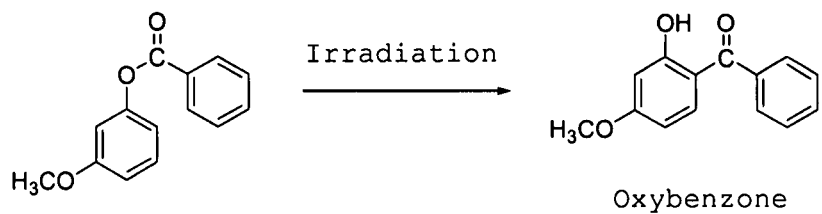

A sample of 5 mg of 3-methoxyphenyl benzoate in 10 mL of polydimethylsiloxane (viscosity 10000 cSt) was irradiated with UVB lamps (60 W·m$^{-2}$) for 15 hours and 20 minutes at 35° C. The phototransformation to oxybenzone was completed in 40 minutes. The phototransposition kinetics is shown in FIG. 6.

Phototransposition Example 7

Phototransposition of 1-phenylvinyl 4-tert-butylbenzoate

A solution of 5 mg of 1-phenylvinyl 4-tert-butylbenzoate in 10 mL of tert-butanol was irradiated with UVB lamps (60 W·m$^{-2}$) for 5 hours at 35° C. Some different compounds were detected by thin layer chromatography (hexane/ethyl acetate 2:1), one of said compounds being benzoyl-4-tert-butylbenzoylmethane, desmethoxyavobenzone, identified by $^1$H-NMR.

Composition Example 1

Sunscreen Composition 1

|  |  |
|---|---|
| Phase A |  |
| Deionized water | 60.0% |
| Disodium EDTA | 0.10% |
| Glycerin | 1.5% |
| NaCl | 3.0% |
| Butylene glycol | 2.5% |
| Phase B |  |
| Active ingredient | 8.75% |
| Octyl salicylate | 5% |
| Aluminum stearate | 5% |
| Cyclomethicone + Dimethicone | 10% |
| Cetyl dimethicone | 1% |
| Cyclomethicone | 2% |
| ABIC-EM 97 | 1% |
| Fragrance | 0.15% |
| TOTAL | 100.00% |

Procedure

Phase B ingredients were combined. The mixture was stirred and heated to 70-75° C. Phase A ingredients were combined. The mixture was heated to 70-75° C. while stirring. Phase B was added to phase A while stirring. Preservative was added. The mixture was stirred, allowing to cool to room temperature.

Composition Example 2

Sunscreen Oil/Water Spray Lotion

|  | % w/w |
|---|---|
| Phase A-1 | |
| Active ingredient 1 | 7.50% |
| Active ingredient 2 | 2.50% |
| Dicapryl ether | 4.50% |
| Dimethicone | 2.00% |
| Stearyl alcohol | 0.60% |
| PPG-2 Ceteareth-9[1] | 0.40% |
| Steareth-10 | 0.50% |
| Glyceryl stearate + PEG-100 stearate[2] | 2.80% |
| Phase A-2 | |
| Titanium dioxide + Simethicone + Alumina[3] | 5.00% |
| Phase B-1 | |
| Demineralized water | 66.10% |
| Chitosan + water[4] | 2.00% |
| Glycerin USP | 2.50% |
| Dimethicone copolyol phosphate | 2.50% |
| Phase B-2 | |
| Polyquaternium 37 + Mineral oil + PPG-1 trideceth-6[5] | 0.40% |
| Phase C | |
| Propylene glycol + DMDM Hydantoin + Methylparaben + Propylparaben[6] | 0.70% |
| TOTAL | 100.00% |

[1]Eumulgin ® L (Henkel)
[2]Ariacel ® 165 (ICI)
[3]Eusolex ® T-2000 (Rona)
[4]Hydagen ® CMF (Henkel)
[5]Salcare ® SC 95 (Ciba)
[6]Paragon ® II (McIntyre)

Procedure

The A-1 ingredients were combined; the mixture was stirred and heated to 60° C. until all solids were dissolved. A-2 was dispersed in A-1 with agitation. The B-1 ingredients were combined; the mixture was stirred and heated to 60° C. B-2 was dispersed in B-1 with agitation. A was added to B while stirring vigorously. The mixture was gently homogenized allowing to cool to 40° C. C was added to A/B; the mixture was gently homogenized until mixture was uniform. The mixture was stirred with another mixer allowing mixture to reach 25° C. prior to packaging. Dispensing is made conveniently by a high shear pump spray device.

Composition Example 3

Sunscreen Cream

|  | % w/w |
|---|---|
| Phase A | |
| Deionized water | 39.73% |
| Carbomer (2% aq. solution) | 15.00% |
| Propylene glycol | 5.00% |
| Methylparaben | 0.20% |
| Propylparaben | 0.10% |
| Triethanolamine (99%) | 0.45% |
| Tetrasodium EDTA | 0.02% |
| Phase B | |
| Active ingredient 1 | 5.00% |
| Active ingredient 2 | 3.00% |
| Active ingredient 3 | 4.50% |
| Glyceryl stearate + PEG-100 stearate[1] | 1.00% |
| Cyclomethicone | 5.00% |
| Glyceryl stearate | 4.00% |
| Stearic acid | 2.50% |
| Isostearyl isostearate | 10.00% |
| Hydrogenated castor oil | 2.00% |
| $C_{12-15}$ alcohol benzoates[2] | 2.50% |
| TOTAL | 100.00% |

[1]Ariacel ® 165 (ICI)
[2]Finsolv ® TN (Finetex)

Procedure

Phase A ingredients were added to a main vessel under impeller agitation. The mixture was heated to 75-80° C. Phase B ingredients were combined; the suspension was heated and mixed to 85° C. Phase B was added slowly to batch and mixed for 15 minutes at 85° C. After removing the mixture from heat, it was switched to paddle mixing and cooled to room temperature.

Composition Example 4

Water/Oil Broad Spectrum Sunscreen Lotion

|  | % w/w |
|---|---|
| Active ingredient 1 | 7.50% |
| Active ingredient 2 | 5.00% |
| Octyl stearate | 2.00% |
| Dicapryl ether | 3.00% |
| Cyclomethicone | 4.00% |
| Dimethicone | 2.00% |
| PEG-30 Dipolyhydroxystearate[1] | 1.30% |
| Laurylmethicone copolyol | 2.30% |
| Behanemidopropyl dimethylamine behenate | 0.50% |
| Titanium dioxide + Alumina + Simethicone[2] | 8.00% |
| Deionized water qs | 61.00% |
| Propylene glycol | 2.00% |
| NaCl | 0.80% |
| Propylene glycol + DMDM Hydantoin + Methylparaben + Propylparaben[3] | 0.60% |
| TOTAL | 100.00% |

[1]Ariacel ® P135 (ICI)
[2]Eusolex ® T-2000 (Rona)
[3]Paragon ® II (McIntyre)

Composition Example 5

UVA/UVB Sun Protection Cream with Avobenzone

| | % w/w |
|---|---|
| Phase A-1 | |
| Water (demineralized) | 67.80% |
| Disodium EDTA | 0.05% |
| Propylene glycol | 3.00% |
| Methylparaben | 0.15% |
| Phase A-2 | |
| Carbomer | 0.20% |
| Phase B | |
| Isopropyl myristate | 2.00% |
| Cetyl alcohol + Glyceryl stearate + PEG-75 Stearate + Cetetch 20 + Steareth 20[1] | 4.00% |
| Active ingredient | 3.50% |
| Homomethyl salicylate | 7.00% |
| Octyl salicylate | 7.00% |
| Avobenzone | 3.00% |
| Dimethicone | 1.00% |
| C30-38 Olefin + Isopropyl maleate + MA copolymer | 1.00% |
| Phase C | |
| Triethanolamine (99%) | 0.30% |
| Phase D | |
| Preservatives | qs |
| TOTAL | 100.00% |

[1]Emulium Delta ® (Gattefosse)
[2]Performa ® V 1608 (New Phase Technologies)

Procedure

Phase A-1 ingredients were combined; the mixture was heated to 50° C. while stirring until methylparaben was dissolved. A-2 was dispersed in A-1 with a sifter. The resulting mixture A was heated to 65° C. Phase B ingredients were combined; the mixture was heated to 65-70° C. while stirring until solids were dissolved. B was added to A. The mixture was homogenized and C was added at 55-60° C. Homogenizing was continued allowing mixture to cool to 40-45° C. Phase D was added; the mixture was stirred with propeller mixer until uniform. pH was adjusted to 6.5-7.0 with triethanolamine.

Composition Example 6

Oil/Water Sunscreen Lotion

| | % w/w |
|---|---|
| Phase A | |
| Active ingredient | 3.00% |
| Isopropyl myristate | 4.00% |
| C$_{12-15}$ Alkyl benzoate[1] | 4.00% |
| Cetyl alcohol | 1.50% |
| Steareth-2 | 2.00% |
| Steareth-21 | 2.50% |
| Dimethicone | 0.50% |
| Phase B | |
| Deionized water | 81.07% |
| Acrylates/C$_{10-30}$ Alkyl Acrylates crosspolymer[2] | 0.20% |
| Phase C | |
| Triethanolamine (99%) | 0.23% |
| Phase D | |
| Phenoxyethanol + Isopropylparaben + Isobutylparaben + Butylparaben[3] | 1.00% |
| TOTAL | 100.00% |

[1]Finsolv ® TN (Finetex)
[2]Carbopol ® ETD 2020 (B F Goodrich)
[3]Liquapar ® PR (Sutton)

Procedure

Phase B was prepared by dispersing Carbopol in water. The dispersion was heated to 70-75° C. Phase A ingredients were combined. The mixture was stirred and heated to 70-75° C. Phase B was added to phase A while stirring. Phase C was added. The mixture was homogenized until it cooled to 45-40° C. Phase D was added. The mixture was stirred allowing to cool to room temperature.

Composition Example 7

Oil/Water Sunscreen Lotion with Avobenzone

| | % w/w |
|---|---|
| Phase A | |
| Active ingredient | 3.00% |
| Avobenzone | 3.00% |
| Isopropyl myristate | 4.00% |
| C$_{12-15}$ Alkyl benzoate[1] | 4.00% |
| Cetyl alcohol | 1.50% |
| Steareth-2 | 2.00% |
| Steareth-21 | 2.50% |
| Dimethicone | 0.50% |
| Phase B | |
| Deionized water | 78.07% |
| Acrylates/C$_{10-30}$ Alkyl Acrylates crosspolymer[2] | 0.20% |
| Phase C | |
| Triethanolamine (99%) | 0.23% |
| Phase D | |
| Phenoxyethanol + Isopropylparaben + Isobutylparaben + Butylparaben[3] | 1.00% |
| TOTAL | 100.00% |

[1]Finsolv ® TN (Finetex)
[2]Carbopol ® ETD 2020 (B F Goodrich)
[3]Liquapar ® PR (Sutton)

Procedure

Phase B was prepared by dispersing Carbopol in water. The dispersion was heated to 70-75° C. Phase A ingredients were combined. The mixture was stirred and heated to 70-75° C. Phase B was added to phase A while stirring. Phase C was added. The mixture was homogenized until it cooled to 45-40° C. Phase D was added. The mixture was stirred allowing to cool to room temperature.

Composition Example 8

Sun Care Lipstick

| | % w/w |
|---|---|
| Active ingredient | 7.00% |
| Microcrystalline wax | 5.00% |
| Glyceryl trihydroxystearate | 5.00% |
| Ozokerite | 3.40% |
| Polyglycerolated beeswax | 2.10% |
| Acetylated lanolin | 19.45% |
| Lanolin oil | 19.10% |
| Avocado oil | 18.99% |
| Butene/isobutene copolymer | 14.34% |
| Castor oil | 4.81% |
| Ascorbyl palmitate | 0.50% |
| Mixture of tocopherols in soybean oil (50/50) | 0.31% |
| TOTAL | 100.00% |

Composition Example 9

Sunscreen Gel

| | % w/w |
|---|---|
| Active ingredient 1 | 8.00% |
| Active ingredient 2 | 6.00% |
| $TiO_2$ | 7.00% |
| Glycerol | 5.00% |
| PEG-25 p-aminobenzoic acid | 5.00% |
| Acrylates/$C_{10-30}$ Alkyl Acrylates crosspolymer[1] | 0.40% |
| Imidazolidinylurea | 0.30% |
| Hydroxyethylcellulose | 0.25% |
| Sodium methylparaben | 0.25% |
| Disodium EDTA | 0.20% |
| Fragrance | 0.15% |
| Sodium propylparaben | 0.15% |
| Sodium hydroxide | 0.10% |
| Water | qs |
| TOTAL | 100.00% |

[1] Carbopol ® ETD 2020 (B F Goodrich)

Composition Example 10

Sunscreen Cream

| | % w/w |
|---|---|
| Active ingredient 1 | 7.00% |
| Active ingredient 2 | 7.00% |
| $TiO_2$ | 8.00% |
| $ZnO_2$ | 5.00% |
| PEG-7 hydrogenated castor oil | 6.00% |
| Mineral oil | 6.00% |
| Isopropyl palmitate | 5.00% |
| Imidazolidinylurea | 0.30% |
| Jojoba oil | 3.00% |
| PEG-45 dodecyl glycol copolymer | 2.00% |
| Magnesium stearate | 0.60% |
| Tocopheryl acetate | 0.50% |
| Methylparaben | 0.25% |
| Disodium EDTA | 0.20% |
| Propylparaben | 0.15% |
| Water | qs |
| TOTAL | 100.00% |

Composition Example 11

Water-Resistant Sunscreen Cream

| | % w/w |
|---|---|
| Active ingredient 1 | 8.00% |
| Active ingredient 2 | 7.00% |
| $TiO_2$ | 3.00% |
| PEG-7 hydrogenated castor oil | 5.00% |
| Propylene glycol | 5.00% |
| Isopropyl palmitate | 4.00% |
| Caprylic/Capric triglyceride | 4.00% |
| Glycerol | 4.00% |
| Jojoba oil | 3.00% |
| PEG-45 dodecyl glycol copolymer | 1.50% |
| Dimethicone | 1.50% |
| Magnesium sulfate | 0.70% |
| Magnesium stearate | 0.50% |
| Fragrance | 0.15% |
| Water | qs |
| TOTAL | 100.00% |

Composition Example 12

Sunscreen Milk

| | % w/w |
|---|---|
| Active ingredient 1 | 4.50% |
| Active ingredient 2 | 4.00% |
| Mineral oil | 10.00% |
| PEG-7 hydrogenated castor oil | 6.00% |
| Isopropyl palmitate | 5.00% |
| Caprylic/Capric triglyceride | 3.00% |
| Jojoba oil | 3.00% |
| PEG-45 dodecyl glycol copolymer | 2.00% |
| Magnesium sulfate | 0.70% |
| Magnesium stearate | 0.60% |
| Tocopheryl acetate | 0.50% |
| Glycerol | 3.00% |
| Methylparaben | 0.25% |
| Propylparaben | 0.15% |
| Tocopherol | 0.05% |
| Water | qs |
| TOTAL | 100.00% |

Composition Example 13

Sunscreen Makeup Powder

|  | % w/w |
| --- | --- |
| Active ingredient 1 | 0.12% |
| Active ingredient 2 | 0.08% |
| Talc | 76.00% |
| Polyethylene powder | 4.00% |
| Magnesium carbonate | 8.76% |
| Isopropyl myristate | 1.20% |
| Liquid petrolatum | 1.20% |
| Sorbitol | 4.00% |
| Bordeaux 5B pigment | 0.52% |
| Victoria Blue Lake pigment | 0.12% |
| Titanium mica | 4.00% |
| TOTAL | 100.00% |

Composition Example 14

Sunscreen Nail Varnish

|  | % w/w |
| --- | --- |
| Active ingredient | 0.30% |
| Nitrocellulose | 6.43% |
| Toluensulfonamide formaldehyde resin | 5.81% |
| Acetyltributyl citrate | 3.83% |
| Butyl acetate | 12.85% |
| Ethyl acetate | 5.54% |
| Stearalkonium hectorite | 0.80% |
| Citric acid | 0.04% |
| Victoria Blue Lake pigment | 0.01% |
| TiO$_2$ | 0.45% |
| Bordeaux 5B pigment | 0.04% |
| Titanium mica | 0.35% |
| Isopropyl alcohol | 4.60% |
| Toluene | qs |
| TOTAL | 100.00% |

The invention claimed is:

1. A method of protecting a human, animal living body or a material from ultraviolet radiation, which comprises treating said human, animal living body or a material with a composition comprising one or more benzoic acid ester compounds of formula (I):

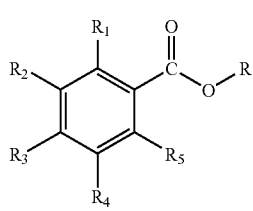

(I)

wherein $R_1$-$R_5$ are selected independently from the group consisting of hydrogen, $C_1$-$C_6$-alkyl, $C_3$-$C_6$-cycloalkyl, $C_1$-$C_6$-alkoxy, $C_3$-$C_6$-cycloalkoxy, hydroxy, amino, $C_1$-$C_6$-alkylamino, and $C_1$-$C_6$-dialkylamino, wherein said two alkyl portions of said dialkylamino can form, together with the nitrogen atom to which they are attached, a heterocycle selected from the group consisting of pyrrolidine, piperidine, morpholine and piperazine optionally N-substituted by $C_1$-$C_6$-alkyl or $C_3$-$C_6$-cycloalkyl, $C_3$-$C_6$-cycloalkylamino, $C_1$-$C_6$-alkyl-$C_3$-$C_6$-cycloalkylamino and $C_3$-$C_6$-dicycloalkylamino, or two groups on adjacent ring carbons form a fused O—(CH$_2$)$_m$—O group wherein m is 1 or 2, or two groups on adjacent ring carbons form a fused CH=CH—CH=C group;

R is a group selected from the group consisting of (i), (ii) and (iii):

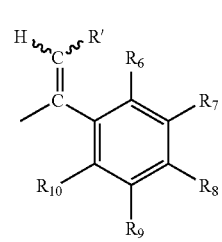

(i)

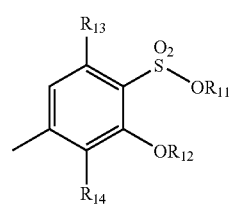

(ii)

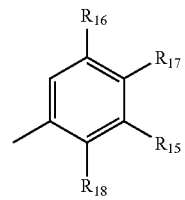

(iii)

wherein R' is selected from the group consisting of hydrogen, $C_1$-$C_6$-alkyl and $C_3$-$C_6$-cycloalkyl;

$R_6$-$R_{10}$ are selected independently from the group consisting of hydrogen, $C_1$-$C_6$-alkyl, $C_3$-$C_6$-cycloalkyl, $C_1$-$C_6$-alkoxy, $C_3$-$C_6$-cycloalkoxy, hydroxy, amino, $C_1$-$C_6$-alkylamino, and $C_1$-$C_6$-dialkylamino, wherein said two alkyl portions of said dialkylamino can form, together with the nitrogen atom to which they are attached, a heterocycle selected from the group consisting of pyrrolidine, piperidine, morpholine and piperazine optionally N-substituted by $C_1$-$C_6$-alkyl or $C_3$-$C_6$-cycloalkyl, $C_3$-$C_6$-cycloalkylamino, $C_1$-$C_6$-alkyl-$C_3$-$C_6$-cycloalkylamino and $C_3$-$C_6$-dicycloalkylamino, or two groups on adjacent ring carbons form a fused O—(CH$_2$)$_n$—O group wherein n is 1 or 2, or two groups on adjacent ring carbons form a fused CH=CH—CH=CH group;

$R_{11}$ is selected from the group consisting of hydrogen, $C_1$-$C_6$-alkyl and $C_3$-$C_6$-cycloalkyl;

$R_{12}$ is selected from the group consisting of hydrogen, $C_1$-$C_6$-alkyl and $C_3$-$C_6$-cycloalkyl;

$R_{13}$ and $R_{14}$ are selected independently from the group consisting of hydrogen, $C_1$-$C_6$-alkyl, $C_3$-$C_6$-cycloalkyl, $C_1$-$C_6$-alkoxy, $C_3$-$C_6$-cycloalkoxy, hydroxy, amino, $C_1$-$C_6$-alkylamino, and $C_1$-$C_6$-dialkylamino, wherein said two alkyl portions of said dialkylamino can form, together with the nitrogen atom to which they are attached, a heterocycle selected from the group consisting of pyrrolidine, piperidine, morpholine and piperazine optionally N-substituted by $C_1$-$C_6$-alkyl or $C_3$-$C_6$-cycloalkyl, $C_3$-$C_6$-cycloalkylamino, $C_1$-$C_6$-alkyl-$C_3$-$C_6$-cycloalkylamino and $C_3$-$C_6$-dicycloalkylamino;

or the group $OR_{12}$ and $R_{14}$ form a fused O—$(CH_2)_p$—O group wherein p is 1 or 2; and $R_{15}$-$R_{18}$ are selected independently from the group consisting of hydrogen, $C_1$-$C_6$-alkyl, $C_3$-$C_6$-cycloalkyl, $C_1$-$C_6$-alkoxy, $C_3$-$C_6$-cycloalkoxy, hydroxy, amino, $C_1$-$C_6$-alkylamino, and $C_1$-$C_6$-dialkylamino, wherein said two alkyl portions of said dialkylamino can form, together with the nitrogen atom to which they are attached, a heterocycle selected from the group consisting of pyrrolidine, piperidine, morpholine and piperazine optionally N-substituted by $C_1$-$C_6$-alkyl or $C_3$-$C_6$-cycloalkyl, $C_3$-$C_6$-cycloalkylamino, $C_1$-$C_6$-alkyl-$C_3$-$C_6$-cycloalkylamino and $C_3$-$C_6$-dicycloalkylamino, or two groups on adjacent ring carbons form a fused O—$(CH_2)_q$—O group wherein q is 1 or 2, or two groups on adjacent ring carbons form a fused CH=CH—CH=CH group;

with the proviso that when $R_1$, $R_2$, and $R_4$-$R_{10}$ are each hydrogen, $R_3$ cannot be hydrogen or methoxy; and with the proviso that when $R_1$-$R_7$, $R_9$ and $R_{10}$ are each hydrogen, $R_8$ cannot be methyl;

or a pharmaceutically acceptable salt thereof, in an effective amount for protecting a human or animal living body or a material from ultraviolet radiation.

2. The method of claim 1, wherein in the benzoic acid ester compound, when R is (i), $R_3$ is selected independently from the group consisting of methoxy and tert-butyl, $R_8$ is selected independently from the group consisting of hydrogen, methoxy and tert-butyl, and R', $R_1$, $R_2$, $R_4$, $R_5$, $R_6$, $R_7$, $R_9$ and $R_{10}$ are each hydrogen;

when R is (ii), $R_1$, $R_2$, $R_3$, $R_4$, $R_5$, $R_{11}$, $R_{13}$ and $R_{14}$ are each hydrogen and $R_{12}$ is methyl; and when R is (iii), $R_1$ is selected independently from the group consisting of hydrogen and hydroxy, $R_3$ is selected independently from the group consisting of hydrogen and methoxy, $R_{15}$ is selected independently from the group consisting of hydrogen, diethylamino, 1-pyrrolidinyl and methoxy, and $R_2$, $R_4$, $R_5$, $R_{16}$, $R_{17}$ and $R_{18}$ are each hydrogen.

3. The method of claim 2, wherein the benzoic acid ester compound is selected from the group consisting of:

1-phenylvinyl 4-methoxybenzoate;

1-(4-methoxyphenyl)-vinyl 4-tert-butylbenzoate;

1-(4-tert-butylphenyl)-vinyl 4-methoxybenzoate;

1-phenylvinyl 4-tert-butylbenzoate;

4-benzoyloxy-2-methoxybenzenesulfonic acid;

3-diethylaminophenyl benzoate;

3-(1-pyrrolidinyl)phenyl benzoate;

3-methoxyphenyl benzoate;

phenyl 4-methoxysalicylate; and 3-methoxyphenyl salicylate.

4. A cosmetic or pharmaceutical composition, a personal care composition or an industrial composition comprising one or more benzoic acid ester compounds of formula (I):

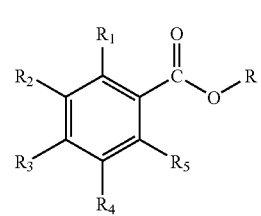

(I)

wherein $R_1$-$R_5$ are selected independently from the group consisting of hydrogen, $C_1$-$C_6$-alkyl, $C_3$-$C_6$-cycloalkyl, $C_1$-$C_6$-alkoxy, $C_3$-$C_6$-cycloalkoxy, hydroxy, amino, $C_1$-$C_6$-alkylamino, and $C_1$-$C_6$-dialkylamino, wherein said two alkyl portions of said dialkylamino can form, together with the nitrogen atom to which they are attached, a heterocycle selected from the group consisting of pyrrolidine, piperidine, morpholine and piperazine optionally N-substituted by $C_1$-$C_6$-alkyl or $C_3$-$C_6$-cycloalkyl, $C_3$-$C_6$-cycloalkylamino, $C_1$-$C_6$-alkyl-$C_3$-$C_6$-cycloalkylamino and $C_3$-$C_6$-dicycloalkylamino, or two groups on adjacent ring carbons form a fused O—$(CH_2)_m$—O group wherein m is 1 or 2, or two groups on adjacent ring carbons form a fused CH=CH—CH=CH group;

R is a group selected from (i), (ii) and (iii):

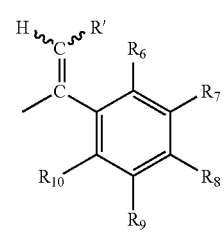

(i)

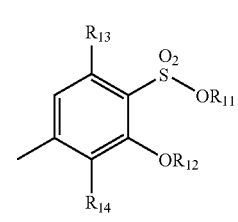

(ii)

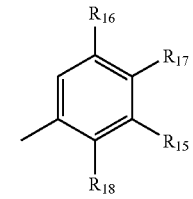

(iii)

wherein R' is selected from the group consisting of hydrogen, $C_1$-$C_6$-alkyl and $C_3$-$C_6$-cycloalkyl;

$R_6$-$R_{10}$ are selected independently from the group consisting of hydrogen, $C_1$-$C_6$-alkyl, $C_3$-$C_6$-cycloalkyl, $C_1$-$C_6$-alkoxy, $C_3$-$C_6$-cycloalkoxy, hydroxy, amino, $C_1$-$C_6$-alkylamino, and $C_1$-$C_6$-dialkylamino, wherein said two alkyl portions of said dialkylamino can form, together with the nitrogen atom to which they are attached, a heterocycle selected from the group consisting of pyrrolidine, piperidine, morpholine and piperazine optionally N-substituted by $C_1$-$C_6$-alkyl or $C_3$-$C_6$-cycloalkyl, $C_3$-$C_6$-cycloalkylamino, $C_1$-$C_6$-alkyl-$C_3$-$C_6$-cycloalkylamino and $C_3$-$C_6$-dicycloalkylamino, or two groups on adjacent ring carbons form a fused O—$(CH_2)_n$—O group wherein n is 1 or 2, or two groups on adjacent ring carbons form a fused CH=CH—CH=CH group;

$R_{11}$ is selected from the group consisting of hydrogen, $C_1$-$C_6$-alkyl and $C_3$-$C_6$-cycloalkyl;

$R_{12}$ is selected from the group consisting of hydrogen, $C_1$-$C_6$-alkyl and $C_3$-$C_6$-cycloalkyl;

$R_{13}$ and $R_{14}$ are selected independently from the group consisting of hydrogen, $C_1$-$C_6$-alkyl, $C_3$-$C_6$-cycloalkyl, $C_1$-$C_6$-alkoxy, $C_3$-$C_6$-cycloalkoxy, hydroxy, amino, $C_1$-$C_6$-alkylamino, and $C_1$-$C_6$-dialkylamino, wherein said two alkyl portions of said dialkylamino can form, together with the nitrogen atom to which they are attached, a heterocycle selected from the group consisting of pyrrolidine, piperidine, morpholine and piperazine optionally N-substituted by $C_1$-$C_6$-alkyl or $C_3$-$C_6$-cycloalkyl, $C_3$-$C_6$-cycloalkylamino, $C_1$-$C_6$-alkyl-$C_3$-$C_6$-cycloalkylamino and $C_3$-$C_6$-dicycloalkylamino;

or the group $OR_{12}$ and $R_{14}$ form a fused O—$(CH_2)_p$—O group wherein p is 1 or 2;

$R_{15}$ is selected from diethylamino, 1-pyrrolidinyl, 1-piperidinyl, 4-morpholinyl and 1(4)-piperazinyl optionally 4(1)-substituted by $C_1$-$C_6$-alkyl or $C_3$-$C_6$-cycloalkyl; and $R_{16}$-$R_{18}$ are selected independently from the group consisting of hydrogen, $C_1$-$C_6$-alkyl, $C_3$-$C_6$-cycloalkyl, $C_1$-$C_6$-alkoxy, $C_3$-$C_6$-cycloalkoxy, hydroxy, amino, $C_1$-$C_6$-alkylamino, and $C_1$-$C_6$-dialkylamino, wherein said two alkyl portions of said dialkylamino can form, together with the nitrogen atom to which they are attached, a heterocycle selected from the group consisting of pyrrolidine, piperidine, morpholine and piperazine optionally N-substituted by $C_1$-$C_6$-alkyl or $C_3$-$C_6$-cycloalkyl, $C_3$-$C_6$-cycloalkylamino, $C_1$-$C_6$-alkyl-$C_3$-$C_6$-cycloalkylamino and $C_3$-$C_6$-dicycloalkylamino, or two groups on adjacent ring carbons form a fused O—$(CH_2)_q$—O group wherein q is 1 or 2, or two groups on adjacent ring carbons form a fused CH=CH—CH=CH group;

with the proviso that when $R_1$, $R_2$, and $R_4$-$R_{10}$ are each hydrogen, $R_3$ cannot be hydrogen or methoxy; and with the proviso that when $R_1$-$R_7$, $R_9$ and $R_{10}$ are each hydrogen, $R_8$ cannot be methyl;

or a pharmaceutically acceptable salt thereof, in an amount effective for protecting a human or animal living body or a material from ultraviolet radiation.

5. The cosmetic or pharmaceutical composition of claim 4, which comprises an effective amount of at least the benzoic acid ester compound, which is susceptible to be photochemically converted in situ to a sunscreen compound with enhanced UV protection ability.

6. The cosmetic or pharmaceutical composition of claim 5, wherein said composition is selected from the group consisting of creams, ointments, milks, suspensions, powders, oils, lotions, gels, sticks, foams, emulsions, dispersions, sprays, aerosols, lipsticks, foundations, makeup, loose or press powders, eye blushes, eye shadows, mascaras, nail varnishes, nail lacquers, and non permanent dyeing compositions for the hair.

7. The method of claim 1, wherein the composition causes a progressive UV protection depending on the time to sun exposition and the degree of sun radiation.

8. The method of claim 7, wherein said composition is selected from the group consisting of creams, ointments, milks, suspensions, powders, oils, lotions, gels, sticks, foams, emulsions, dispersions, sprays, aerosols, lipsticks, foundations, makeup, loose or press powders, eye blushes, eye shadows, mascaras, nail varnishes, nail lacquers and non permanent dyeing compositions for the hair.

9. The method of claim 8, wherein the effective amount of the benzoic acid ester compound ranges from 0.01 to 40 wt % based on the total weight of the sunscreen.

10. The personal care composition of claim 4, wherein said composition is selected from the group consisting of creams, ointments, milks, suspensions, powders, oils, lotions, gels, sticks, foams, emulsions, dispersions, sprays, aerosols, lipsticks, foundations, makeup, loose or press powders, eye blushes, eye shadows, mascaras, nail varnishes, nail lacquers and non permanent dyeing compositions for the hair.

11. The method of claim 1, wherein said material is selected from the group consisting of organic compounds, oils, fats, waxes, gelatins, sunscreens, polymers, radiation curable compositions, resins, varnishes, cellulose, cellulose-based paper formulations, photographic materials, photographic film paper, metallic products, ceramic products, biocides, natural textile fibers, textile fabrics, dyes, inks, pigments, paints, coatings, adhesives, leathers, woods, rubbers, glasses, lenses, composites, mixtures and blends thereof.

12. A method of claim 11, which comprises an effective amount of at least a benzoic acid ester compound susceptible to be photochemically converted in situ to a sunscreen compound with enhanced UV protection ability.

13. The method of claim 12, wherein the effective amount of the benzoic acid ester compound ranges from 0.01 to 30% by weight, based on the weight of the material to be stabilized.

14. The method of claim 11, wherein said polymers are selected from the group consisting of polyolefins, polyketones, polystyrene, polyvinyl chloride (PVC), polyacrylates, polymethacrylates, polyacrylamides, polyacrylonitriles, polyvinyl alcohol derivatives, polyvinyl acetate derivatives, polyurethanes, polyamides, polyesters, polyureas, polycarbonates, polysiloxanes, polyketimines, composites, mixtures and blends thereof.

15. The method of claim 11, wherein said resins are selected from the group consisting of hydrocarbon resins, phenol/formaldehyde resins, urea/formaldehyde resins, melamine/formaldehyde resins, unsaturated polyester resins, crosslinkable acrylic resins, crosslinkated epoxy resins, epoxy/melamine resins, composites, mixtures and blends thereof.

16. The method claim 11, wherein said naturals textile fibers are selected from the group consisting of silk, cotton and wool, composites, mixtures and blends thereof.

17. A benzoic acid ester compound of formula (Ia):

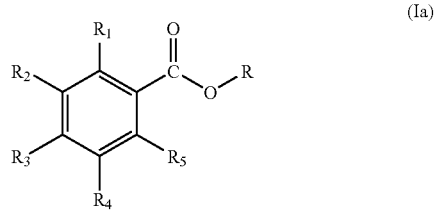

wherein R is a group selected from the group consisting of (i), (ii) and (iii):

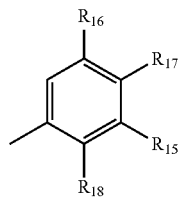

wherein $R_1$-$R_5$ are selected independently from the group consisting of hydrogen, $C_1$-$C_6$-alkyl, $C_3$-$C_6$-cycloalkyl, $C_1$-$C_6$-alkoxy, $C_3$-$C_6$-cycloalkoxy, hydroxy, amino, $C_1$-$C_6$-alkylamino, and $C_1$-$C_6$-dialkylamino, wherein said two alkyl portions of said dialkylamino can form, together with the nitrogen atom to which they are attached, a heterocycle selected from the group consisting of pyrrolidine, piperidine, morpholine and piperazine optionally N-substituted by $C_1$-$C_6$-alkyl or $C_3$-$C_6$-cycloalkyl, $C_3$-$C_6$-cycloalkylamino, $C_1$-$C_6$-alkyl-$C_3$-$C_6$-cycloalkylamino, or $C_3$-$C_6$-dicycloalkylamino, or two groups on adjacent ring carbons form a fused O—$(CH_2)_m$—O group wherein m is 1 or 2, or two groups on adjacent ring carbons form a fused CH=CH—CH=CH group;

R' is hydrogen;

$R_6$-$R_{10}$ are selected independently from the group consisting of hydrogen, $C_1$-$C_6$-alkyl, $C_3$-$C_6$-cycloalkyl, $C_1$-$C_6$-alkoxy, $C_3$-$C_6$-cycloalkoxy, hydroxy, amino, $C_1$-$C_6$-alkylamino, and $C_1$-$C_6$-dialkylamino, wherein said two alkyl portions of said dialkylamino can form, together with the nitrogen atom to which they are attached, a heterocycle selected from the group consisting of pyrrolidine, piperidine, morpholine and piperazine optionally N-substituted by $C_1$-$C_6$-alkyl or $C_3$-$C_6$-cycloalkyl, $C_3$-$C_6$-cycloalkylamino, $C_1$-$C_6$-alkyl-$C_3$-$C_6$-cycloalkylamino and $C_3$-$C_6$-dicycloalkylamino, or two groups on adjacent ring carbons form a fused O—$(CH_2)_n$—O group wherein n is 1 or 2, or two groups on adjacent ring carbons form a fused CH=CH—CH=CH group;

$R_{11}$ is selected from the group consisting of hydrogen, $C_1$-$C_6$-alkyl and $C_3$-$C_6$-cycloalkyl;

$R_{12}$ is selected from the group consisting of hydrogen, $C_1$-$C_6$-alkyl and $C_3$-$C_6$-cycloalkyl;

$R_{13}$ and $R_{14}$ are selected independently from the group consisting of hydrogen, $C_1$-$C_6$-alkyl, $C_3$-$C_6$-cycloalkyl, $C_1$-$C_6$-alkoxy, $C_3$-$C_6$-cycloalkoxy, hydroxy, amino, $C_1$-$C_6$-alkylamino, and $C_1$-$C_6$-dialkylamino, wherein said two alkyl portions of said dialkylamino can form, together with the nitrogen atom to which they are attached, a heterocycle selected from the group consisting of pyrrolidine, piperidine, morpholine and piperazine optionally N-substituted by $C_1$-$C_6$-alkyl or $C_3$-$C_6$-cycloalkyl, $C_3$-$C_6$-cycloalkylamino, $C_1$-$C_6$-alkyl-$C_3$-$C_6$-cycloalkylamino and $C_3$-$C_6$-dicycloalkylamino;

or the group $OR_{12}$ and $R_{14}$ form a fused O—$(CH_2)_p$—O group wherein p is 1 or 2;

$R_{15}$ is selected from the group consisting of 1-pyrrolidinyl, 1-piperidinyl, 4-morpholinyl and 1(4)-piperazinyl optionally 4(1)-substituted by $C_1$-$C_6$-alkyl or $C_3$-$C_6$-cycloalkyl; and $R_{16}$-$R_{18}$ are selected independently from the group consisting of hydrogen, $C_1$-$C_6$-alkyl, $C_3$-$C_6$-cycloalkyl, $C_1$-$C_6$-alkoxy, $C_3$-$C_6$-cycloalkoxy, hydroxy, amino, $C_1$-$C_6$-alkylamino, and $C_1$-$C_6$-dialkylamino, wherein said two alkyl portions of said dialkylamino can form, together with the nitrogen atom to which they are attached, a heterocycle selected from the group consisting of pyrrolidine, piperidine, morpholine and piperazine optionally N-substituted by $C_1$-$C_6$-alkyl or $C_3$-$C_6$-cycloalkyl, $C_3$-$C_6$-cycloalkylamino, $C_1$-$C_6$-alkyl-$C_3$-$C_6$-cycloalkylamino and $C_3$-$C_6$-dicycloalkylamino, or two groups on adjacent ring carbons form a fused O—$(CH_2)_q$—O group wherein q is 1 or 2, or two groups on adjacent ring carbons form a fused CH=CH—CH=CH group;

with the proviso that when $R_1$, $R_2$, and $R_4$-$R_{10}$ are each hydrogen, $R_3$ cannot be hydrogen or methoxy; and with the proviso that when $R_1$-$R_7$, $R_9$ and $R_{10}$ are each hydrogen, $R_8$ cannot be methyl;

or a pharmaceutically acceptable salt thereof.

18. The benzoic acid ester compound of claim 17, wherein in said compound, when R is (i), $R_3$ is selected independently from the group consisting of $C_1$-$C_6$-alkyl, $C_3$-$C_6$-cycloalkyl, $C_1$-$C_6$-alkoxy, $C_3$-$C_6$-cycloalkoxy, $R_8$ is selected independently from the group consisting of hydrogen, $C_1$-$C_6$-alkyl, $C_3$-$C_6$-cycloalkyl, $C_1$-$C_6$-alkoxy and $C_3$-$C_6$-cycloalkoxy, and $R_1$, $R_2$, $R_4$-$R_7$, $R_9$ and $R_{10}$ are each hydrogen;

when R is (ii), $R_1$-$R_5$, $R_{11}$, $R_{13}$ and $R_{14}$ are each hydrogen and $R_{12}$ is $C_1$-$C_6$-alkyl and $C_3$-$C_6$-cycloalkyl; and when R is (iii), $R_{15}$ is selected from the group consisting of 1-pyrrolidinyl, 1-piperidinyl, 4-morpholinyl and 1(4)-piperazinyl optionally 4(1)-substituted by $C_1$-$C_6$-alkyl or $C_3$-$C_6$-cycloalkyl and $R_{16}$-$R_{18}$ are each hydrogen;

with the proviso that when $R_1$, $R_2$, and $R_4$-$R_{10}$ are each hydrogen, $R_3$ cannot be hydrogen or methoxy; and with the proviso that when $R_1$-$R_7$, $R_9$ and $R_{10}$ are each hydrogen, $R_8$ cannot be methyl;

or a pharmaceutically acceptable salt thereof.

19. A benzoic acid ester compound, wherein said compound is selected from the group consisting of:

1-(4-methoxyphenyl)-vinyl 4-tert-butylbenzoate;

1-(4-tert-butylphenyl)-vinyl 4-methoxybenzoate;

1-phenylvinyl 4-tert-butylbenzoate;

4-benzoyloxy-2-methoxybenzenesulfonic acid; and 3-(1-pyrrolidinyl)phenyl benzoate.

20. A process to prepare a benzoic acid ester compound as defined in claim 17, wherein R is (i), by reacting an acyl halide of formula (II):

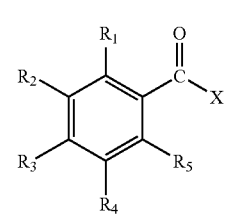

wherein $R_1$-$R_5$ are as defined above, and X is an halogen atom selected from the group consisting of fluorine, chlorine and bromine, with a silylenol of formula (III):

(III)

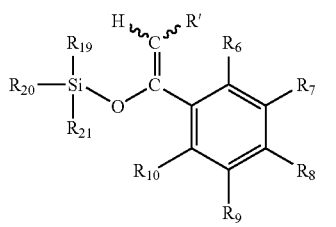

wherein R' and $R_6$-$R_{10}$ are as defined above and $R_{19}$-$R_{21}$ are selected independently from the group consisting of $C_1$-$C_6$-alkyl, $C_3$-$C_6$-cycloalkyl and $C_6H_5$—$(CH_2)_r$—, wherein r is 1-4, or two groups can form, together with the silicium atom a ring selected from the group consisting of silolane, sililane and silepane, in the presence of a catalyst selected from the group consisting of mercuric chloride, cuprous chloride and mixtures thereof.

21. The process according to claim 20, wherein X is chlorine and $R_{19}$-$R_{21}$ are each methyl.

22. A process to prepare a benzoic acid ester compound as defined in claim 17, wherein R is (ii), by reacting a benzoic acid ester of formula (IV):

(IV)

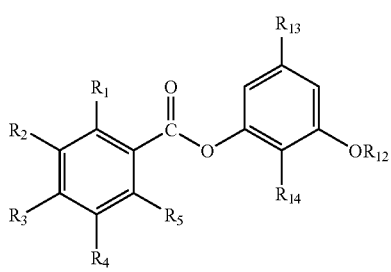

wherein $R_1$-$R_5$ and $R_{12}$-$R_{14}$ are as defined above, with chlorosulfonic acid followed by an optional esterification reaction with $C_1$-$C_6$-alkyl-OH or $C_3$-$C_6$-cycloalkyl-OH.

23. A process to prepare a benzoic acid ester compound as defined in claim 17, wherein R is (ii) and $R_{11}$ is hydrogen, by esterifying an intermediate (VI):

(VI)

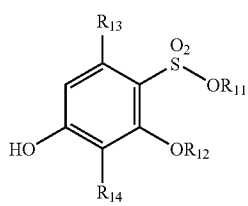

wherein $R_{11}$ is hydrogen and $R_{12}$-$R_{14}$ are as defined above, with an acid intermediate (VII):

(VII)

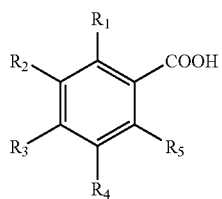

wherein $R_1$-$R_5$ are as defined above.

24. A process to prepare a benzoic acid ester compound as defined in claim 17, wherein R is (ii), by esterifying the intermediate (VI):

(VI)

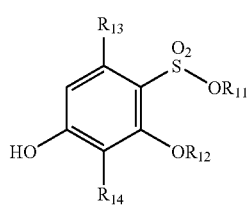

wherein $R_{11}$ is $C_1$-$C_6$-alkyl or $C_3$-$C_6$-cycloalkyl and $R_{12}$-$R_{14}$ are as defined above, with (VII).

25. A process to prepare a benzoic acid ester compound as defined in claim 17, wherein R is (iii), by reacting an acyl halide of formula (II):

(II)

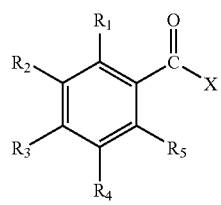

wherein $R_1$-$R_5$ are as defined above, and X is an halogen atom selected from the group consisting of fluorine, chlorine and bromine, with a phenol of formula (VIII):

(VIII)

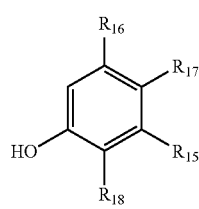

wherein $R_{15}$-$R_{18}$ are as defined above.

* * * * *